United States Patent [19]

Safe

[11] Patent Number: 5,516,790
[45] Date of Patent: May 14, 1996

[54] SYNTHESIS AND APPLICATION OF ALKYL-SUBSTITUTED DIBENZOFURANS AS ANTITUMORIGENIC AGENTS

[75] Inventor: Stephen H. Safe, College Station, Tex.

[73] Assignee: Texas A&M University System Technology Licensing Office, College Station, Tex.

[21] Appl. No.: 275,734

[22] Filed: Jul. 19, 1994

Related U.S. Application Data

[63] Continuation of Ser. No. 947,850, Sep. 21, 1992, abandoned, which is a continuation-in-part of Ser. No. 639,551, Jan. 10, 1991, abandoned, which is a continuation of Ser. No. 300,416, Jan. 23, 1989, abandoned.

[51] Int. Cl.⁶ .................................................... A61K 31/34
[52] U.S. Cl. ........................... 514/443; 549/388; 549/460
[58] Field of Search .............................. 514/443; 549/460

[56] References Cited

U.S. PATENT DOCUMENTS

| | | | |
|---|---|---|---|
| 2,500,734 | 3/1950 | Abbott, Jr. | 260/346 |
| 2,648,684 | 8/1953 | Wenner | 260/346.2 |
| 3,108,121 | 10/1963 | Walsh et al. | 260/346.2 |
| 3,251,859 | 5/1966 | Kulka et al. | 260/340.3 |
| 3,649,651 | 3/1972 | Dobson | 260/346.2 |
| 3,679,704 | 7/1972 | Lester et al. | 260/340.3 |
| 3,751,390 | 8/1973 | Hopps et al. | 260/297 |
| 3,812,152 | 5/1974 | Hofer et al. | 260/329.3 |
| 3,840,593 | 10/1974 | Sidwell | 260/561 |
| 3,906,007 | 9/1975 | Albrecht et al. | 260/346.2 |
| 3,920,635 | 11/1975 | Nysted | 260/239.57 |
| 3,935,251 | 1/1976 | Dazzi | 260/346 |
| 3,939,155 | 2/1976 | Brown | 260/239 |
| 3,989,761 | 11/1976 | Gross | 260/620 |
| 4,000,203 | 12/1976 | Gross et al. | 260/620 |
| 4,009,185 | 2/1977 | Fishel | 260/346.2 |
| 4,010,268 | 3/1977 | Matharu et al. | 424/250 |
| 4,013,694 | 3/1977 | Fishel | 260/346.2 |
| 4,042,603 | 8/1977 | Itatani et al. | 260/346 |
| 4,058,516 | 11/1977 | Mislin et al. | 260/152 |
| 4,065,469 | 12/1977 | Moggi et al. | 260/346.71 |
| 4,228,309 | 11/1980 | Hatcher | 568/755 |
| 4,273,771 | 6/1981 | Coussediere | 424/242 |
| 4,293,707 | 10/1981 | Richter et al. | 562/472 |
| 4,306,098 | 12/1981 | Brooker | 568/776 |
| 4,326,882 | 4/1982 | Richter et al. | 562/472 |
| 4,362,883 | 12/1982 | Harvey | 549/460 |
| 4,376,776 | 3/1983 | Rentzea et al. | 424/267 |
| 4,418,068 | 11/1983 | Jones | 424/267 |
| 4,467,117 | 8/1984 | Lund et al. | 568/637 |
| 4,486,610 | 12/1984 | Lund | 568/637 |
| 4,490,562 | 12/1984 | Schreiber et al. | 568/637 |
| 4,608,127 | 8/1986 | Sakuma et al. | 203/48 |
| 4,729,999 | 3/1988 | Young | 514/227 |
| 4,732,904 | 3/1988 | Morgan | 514/357 |
| 4,745,109 | 5/1988 | Bednarski et al. | 514/170 |

OTHER PUBLICATIONS

Astroff, et al., The Toxicologist, 9, p. 127 (1989).
Bannister, et al., Toxicology, 54, p. 139 (1989).
Astroff, et al., Toxicol. Appl. Pharmacol, 95, p. 1 (1988).
Romkes, PHd Thesis, Texas A&M Univ., pp. 74, 75, 77–81, 114–118 (88).
Umbreit, et al., Toxicol. Leeters, 42 p. 5 (1988).
Romkes, et al. Toxicol. Appl. Pharmacol., 92, p. 368 (1988).
Holcomb, et al., Biochem. Pharmacol., 37, p. 1535 (1988).
Astroff, et al., Mol. Pharmacol., 33, p. 231 (1988).
Romkes, et al, Toxicol. Appl. Pharmacol., 87, p. 306 (1987).
Gierthy, et al., Cancer Res., 47, p. 6198 (1987).
Bannister, et al., Chemosphere, vol. 16, Nos. 8/9, p. 2739 (1987).
Romkes, et al., Cancer Res., 47, p. 5108 (1987).
Keys, et al., Toxiocl. Letters, 31, p. 151 (1986).
Mason et al., Toxicol, 37, p. 1 (1985).
Denomme, et al., chemc.–Boil. Interactions, 57, p. 175 (1986).
Mason, et al., Toxicol., 37, p. 1 (1985).
Denomme, et al, Molec. Pharmacol, 27, p. 656 (1985).
Safe et al., Agricul. Food Chem., 32, p. 68 (1984).
Shiverick, et al., Toxicol. Appl. Pharmacol, 65, p. 170 (1982).
Kociba, et al, Toxicol. Appl. Pharmacol, 65, p. 170 (1982).
Ramalingan et al., Chlorinated Dioxins Dibenzofurens Perspect., 1986, pp. 485–499.
Gray et al., J. Org. Chem., 41, 2428 (!976).
Denome et al., Chem.–Biol. Interactions, 57, 175–187 (1986) (of record in the parent application).
Astroff et al., C. A., 110:19,507gf (1989)—Abstract of Toxical. Appl. Pharmacol., 95(3), 435–433 (1988).
Yao et al., C. A., 111: 168,9646 (1989)–Abstract of Toxxical. Appl. Pharmacol., 100(2), 208–16 (1989).
Harris et al., C.A., 111: 51,858d (1989)–Abstract of Mol. Pharmecol., 35(5), 729–35 (1989).

*Primary Examiner*—Nicky Chan
*Attorney, Agent, or Firm*—Baker & Botts; Patrick Turley

[57] ABSTRACT

Provided is a method of inhibiting estrogen activity by administering a biologically active amount of a substituted dibenzofuran or substituted dibenzodioxin.

16 Claims, No Drawings

SYNTHESIS AND APPLICATION OF ALKYL-SUBSTITUTED DIBENZOFURANS AS ANTITUMORIGENIC AGENTS

This application is a continuation of application Ser. No. 07/947,850, filed Sep. 21, 1992, now abandoned, which is a continuation-in-part of application Ser. No. 07/639,551, filed Jan. 10, 1991, now abandoned, which is a continuation of application Ser. No. 07/300,416, filed Jan. 23, 1989, now abandoned.

BACKGROUND OF THE INVENTION

This invention relates to alkyl- and/or halo-substituted dibenzofurans and to substituted dibenzo-p-dioxins and to methods of preparing such compounds. It further relates to the use of the compounds as antiestrogenics and to pharmaceutical compositions containing said compounds.

Antiestrogens are a class of chemicals which inhibit estrogens from eliciting their full response in target tissues. They can be used to explore the mechanisms of action of estrogens and to provide treatment for estrogen-dependent diseases (e.g., tumors). An antiestrogenic compound currently being utilized in the treatment of mammary cancer is tamoxifen. Progesterone and related progestins have also been used extensively to treat mammary cancer in laboratory animals and humans. Numerous other antiestrogens have been disclosed in recent years including inhibitors of aromatase (Bednarski U.S. Pat. No. 4,745,109), antiestrogenic hydrazones (Morgan U.S. Pat. No. 4,732,904) and antiestrogenic benzothiophenes (Jones U.S. Pat. No. 4,418,068).

2,3,7,8-tetrachloridibenzo-p-dioxin (TCDD) is one of the most toxic man-made chemicals. It acts through initial binding to the aryl hydrocarbon (Ah) receptors. Research in the past has focused on the identification and mechanisms of the toxic effects of TCDD in the body and particularly on its induction of aryl hydrocarbon hydroxylase (AHH) and ethoxyresorufin O-deethylase (EROD). Mason et al. Toxicol. 41, 21–31 (1986); Denomme et al. Chem. Biol. Interactions, 57, 175–187 (1986).

Recent studies in several laboratories have reported the activity of TCDD as an antiestrogen in rats, mice and MCF-7 human breast cancer cell lines in culture. For example, TCDD treatment resulted in decreased uterine weights in weanling female C57BL/6 mice and female Long Evans rats and TCDD partially blocked the estrogenic effects of 17β-estradiol on uterine weights. Romkes et al., Toxicol. and Applied Pharm. 87, 306–314 (1987). TCDD also decreased constitutive and 17β-estradiol induced uterine and hepatic estrogen and progesterone receptor levels in the female rat and suppressed the estrogen mediated excretion of tissue plasminogen activator activity in MCF-7 human breast cancer cells in culture. Romkes et al., Toxicol. and Appl. Pharmacol. 92, 368–380 (1988); Gierthy et al., Cancer Research 47, 6198–6203 (1987). Kociba and coworkers reported that after long term feeding studies, TCDD significantly decreased the spontaneous development of mammary and uterine tumors in Female Spraque-Dawley rats. Kociba, Toxicol. and Appl. Pharmacol. 46, 279–303 (1978). However, TCDD is so hepatocarcinogenic that it has not been seriously considered for use as a therapeutic antiestrogenic.

TCDD does not bind to the estrogen receptor and studies suggest, although we do not limit ourselves to this theory, that the antiestrogenic activities of TCDD are mediated through the Ah receptor. Many dibenzo-p-dioxin and dibenzofuran analogs of TCDD also exhibit a binding affinity for the Ah receptor. Recent studies have focused on the identification and mechanism of action of these compounds as TCDD antagonists, particularly in inhibiting TCDD-mediated induction of AHH and EROD in laboratory animals and mammalian cells in culture. (Keys et al., Toxicol. Letters, 31 (1986) 151–158, Astroff et al., Molecular Pharmacol. 33:231–236 (1988).) Studies have particularly focused on 1,3,6,8 and 2,4,6,8-substituted dibenzofurans. The activity of the 2,3,6,8- and 1,3,6,8-substituted dibenzofurans and dibenzo-p-dioxins as Ah receptor agonists (e.g., induction of AHH, thymic atrophy, etc.) was low to non-detectable in most biosystems despite their moderate binding affinity for the Ah receptor.

SUMMARY OF THE INVENTION

The present invention provides for a class of alkyl-substituted and/or halo-substituted compounds, such as, but not limited to, preferably 1,3,6,8 and 2,4,6,8 substituted dibenzofurans and dibenzo-p-dioxins, which are nontoxic at biologically active levels and which are antiestrogens. The compounds can be used pharmaceutically for antiestrogen therapy and particularly for the treatment of estrogen-dependent tumors. This invention further provides for pharmaceutical compositions of the antiestrogenic compounds and for methods of administering the compounds to inhibit estrogen activity and to treat estrogen dependent tumors. In addition, this invention provides a method of producing the alkyl- and/or halo-substituted dibenzofurans and dibenzo-p-dioxins.

A series of 6-methyl 1,3,8-trichlorodibenzofuran (MCDF) analogs in which each of the positions was replaced with a hydrogen, demonstrated TCDD antagonist activity. For most of the compounds, their partial antagonist potential correlated with their competitive binding affinities for the hepatic Ah receptor. Since the presence of a substituent at C-6 is important for antagonist activity, a series of 6-substituted 1,3,8-tricholordibenzofurans were synthesized and their structural activity effects as TCDD antagonists were also determined. All of the 6-substituted acyclic alkyl-substituted analogs were active as TCDD antagonists in vivo and in vitro but showed low agonist activity for AHH and EROD induction. All of these antagonists were at least $10^5$ less active (or toxic) than TCDD and their antagonist activities were observed at subtoxic doses.

Based on previous studies with 6-methyl 1,3,8-trichlorodibenzofuran (MCDF) which have indicated that MCDF is an antagonist to the activities of TCDD, it was expected that this compound would also antagonize the antiestrogenicity of TCDD. However, like TCDD, MCDF caused a dose response decrease in uterine and hepatic cytosolic and nuclear estrogen and progesterone receptor levels. MCDF was also active as an antiestrogen in inhibiting 17β-estradiol-induced increases in rat uterine wet weight. (Astroff and Safe, Toxicol. and Appl. Pharmacol. 95, p. 435–443 (1988)).

The antiestrogenic activities of MCDF were completely unexpected and the reasons that MCDF is a poor agonist for the traditional "Ah receptor mediated response" but a good agonist for the modulation of steroid hormone receptor binding levels are unknown. Therefore, MCDF represents a new class of halogenated aromatic antiestrogens which exhibit relatively high Ah receptor binding activity and low toxicity.

It is an object of the present invention to provide a method of inhibiting estrogen activity comprising administering a biologically active amount of a compound of the formula:

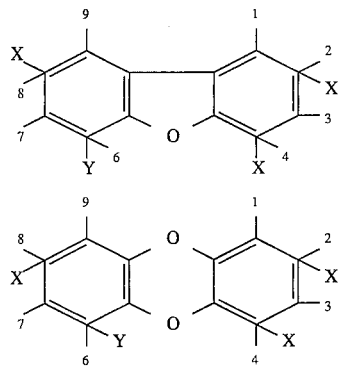

wherein X, individually and independently, is a hydrogen or a substituent selected from the group consisting of bromine, chlorine, fluorine, and a linear or branched alkyl group of about one to about four carbons, with no more than one X being a hydrogen; wherein Y is a substituent selected from the group consisting of bromine, chlorine, fluorine, and a linear or branched alkyl group of about one to about four carbons; said compound having at least one alkyl substituent.

It is an object of the present invention to provide a method of inhibiting estrogen activity comprising administering a biologically active amount of a compound of the formula:

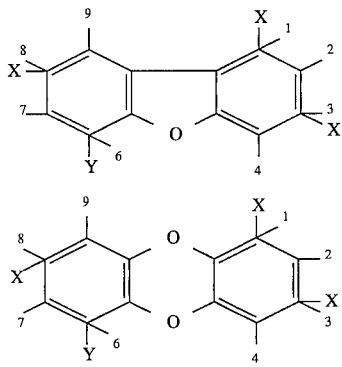

wherein X, individually and independently, is a hydrogen or a substituent selected from the group consisting of bromine, chlorine, fluorine, and a linear or branched alkyl group of about one to about four carbons, with no more than one X being a hydrogen; wherein Y is a substituent selected from the group consisting of bromine, chlorine, fluorine, and a linear or branched alkyl group of about one to about four carbons; said compound having at least one alkyl substituent.

It is an object of the present invention to provide a method of treating estrogen-dependent tumors comprising administering a biologically active amount of a compound of the formula:

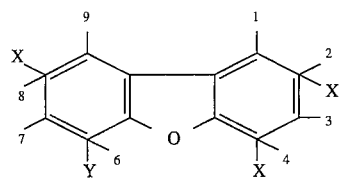

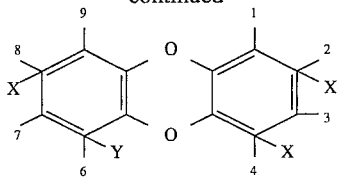

wherein X, individually and independently, is a hydrogen or a substituent selected from the group-consisting of bromine, chlorine, fluorine, and a linear or branched alkyl group of one to four carbons, with no more than one X being a hydrogen; wherein Y is a substituent selected from the group consisting of bromine, chlorine, fluorine, and a linear or branched alkyl group of about one to about four carbons; and said compound having at least one alkyl substituent.

It is the object of the present invention to provide a method of treating estrogen-dependent tumors comprising administering a biologically active amount of a compound of the formula:

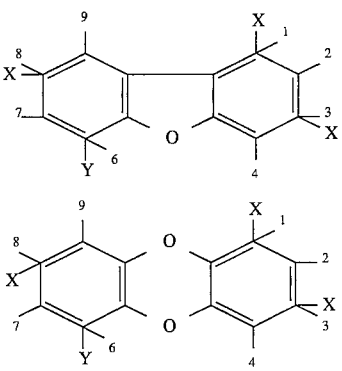

wherein X, individually and independently, is a hydrogen or a substituent selected from the group consisting of bromine, chlorine, fluorine, and a linear or branched alkyl group of about one to about four carbons, with no more than one X being a hydrogen; wherein Y is a substituent selected from the group consisting of bromine, chlorine, fluorine, and a linear or branched alkyl group of about one to about four carbons; and said compound having at least one alkyl substituent.

It is an object of the present invention to provide a composition comprising a biologically active amount of a compound of the formula:

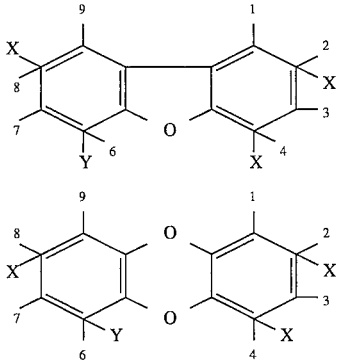

wherein X, individually and independently, is a hydrogen or a substituent selected from the group consisting of bromine, chlorine, fluorine, and a linear or branched alkyl group of about one to about four carbons, with no more than one X being a hydrogen; where Y is a substituent selected from the group consisting of bromine, chlorine, fluorine, and a linear or branched alkyl group of about one to about four carbons; said compound having at least one alkyl substituent; and an appropriate carrier.

It is an object of the present invention to provide a composition comprising a biologically active amount of a compound of the formula:

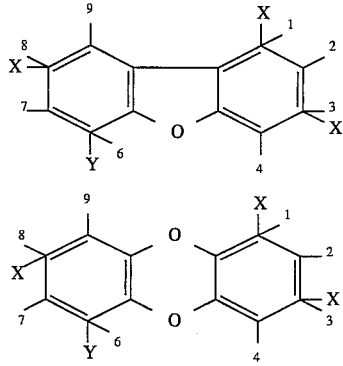

wherein X, individually and independently, is a hydrogen or a substituent selected from the group consisting of bromine, chlorine, fluorine, and a linear or branched alkyl group of about one to about four carbons, with no more than one X being a hydrogen; wherein Y is a substituent selected from the group consisting of bromine, chlorine, fluorine, and a linear or branched alkyl group of about one to about four carbons; said compound having at least one alkyl substituent; and an appropriate carrier.

It is an object of the present invention to provide a method of treating estrogen dependent tumors comprising administering a biologically active amount of a compound of the formula:

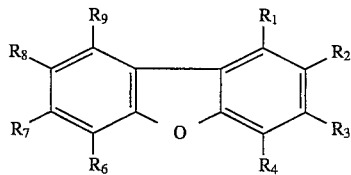

wherein $R_1$, $R_2$, $R_3$, $R_4$, $R_6$, $R_7$, $R_8$ and $R_9$ are individually and independently a hydrogen or a substituent selected from the group consisting of bromine, chlorine, fluorine, and a linear or branched alkyl group of about one to about four carbons; said compound having at least 2 lateral substituents and at least one alkyl substituent.

It is an object of the present invention to provide a composition comprising a biologically active 15 amount of a compound of the formula:

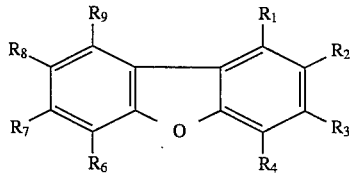

wherein $R_1$, $R_2$, $R_3$, $R_4$, $R_6$, $R_7$, $R_8$ and $R_9$ are individually and independently a hydrogen or a substituent selected from the group consisting of bromine, chlorine, fluorine, and a linear or branched alkyl group of about one to about four carbons; said compound having at least 2 lateral substituents and at least one alkyl substituent.

These and other advantages of the present invention will become apparent from the following detailed description.

DESCRIPTION OF THE PREFERRED EMBODIMENTS

Synthesis of Alkyl-Substituted Dibenzofurans

The starting reactants for alkyl-substituted dibenzofurans are substituted phenols (R=H) or anisoles (R=CH$_3$) and substituted 6-haloanilines or substituted o-aminoanisoles and halobenzenes. The composition of the substituted dibenzofuran end product is dependent upon the positions of the substituents on the substituted phenol/anisole, the substituted haloaniline, the substituted benzene, and the substituted aminoanisole. Because the substituted dibenzofuran is symmetrical through the vertical axis, the end product and the beginning reactants could be renamed for their mirror images. To be consistent, this description will discuss the reactants and the end product as pictured in Diagram 1

Diagram 1

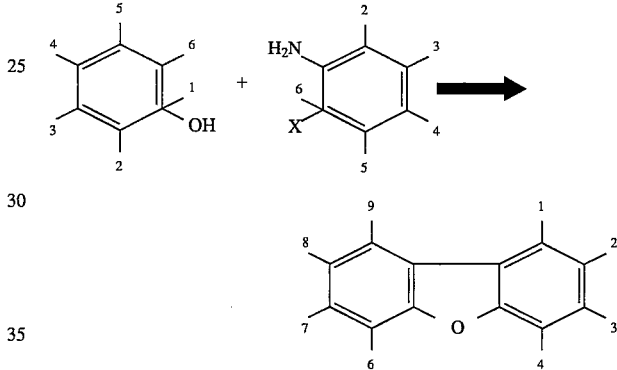

where X is a halogen. The end product shown is a dibenzofuran and the numbers represent positions where substituents may be selectively placed.

The number of substituents at carbon positions 2, 3, 7 and/or 8 indicate the number of lateral substituents. For example, a compound containing substituents at positions 3 and 8 would have 2 lateral substituents, even if positions 1, 4, 6 and/or 9 also contained substituents. A compound containing substituents at positions 2, 3 and 8 would have 3 lateral substituents, even if positions 1, 4, 6 and/or 9 also contained substituents. A compound containing substituents at positions 2, 3, 7 and 8 would have 4 lateral substituents, even if positions 1, 4, 6 and/or 9 also contained substituents. Positions numbered 1, 4, 6 and 9 are the nonlateral positions.

Possible substituents are halogens such as bromine, chlorine, fluorine and/or linear or branched substituents such as alkyl groups of about one to about five carbons. The positions may also be individually and independently occupied by a hydrogen instead of a substituent. In the preferred mode, the halogen substituents of the compound will be chlorine or bromine, the alkyl substituents will be of about one to about four carbon atoms, and the substituents of the reactants will be such that the final substituted dibenzofuran will be substituted with at least one alkyl group, and more preferably with one alkyl group. Suitable alkyl substituents include, but are not limited to, methyl, ethyl, propyl, isopropyl (i-propyl), n-butyl, sec-butyl or tert-butyl groups. The compound will be an alkyl-substituted dibenzofuran having 2, 3, or 4 lateral substituents and will contain at least one alkyl substituent which may be in a lateral or non-lateral position. In the preferred embodiment, the composition for treating estrogen-dependent tumors can be depicted as:

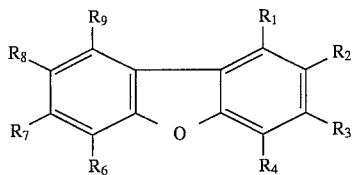

wherein $R_1$, $R_2$, $R_3$, $R_4$, $R_6$, $R_7$, $R_8$ and $R_9$ are individually and independently a hydrogen or a substituent selected from the group consisting of bromine, chlorine, fluorine, and a linear or branched alkyl group of about one to about four carbons; said compound having at least 2 lateral substituents and at least one alkyl substituent.

The substituted phenol (100 mmol) and substituted 6-haloaniline (20 mmol) are mixed and heated with stirring at 120°–130° C. Isoamyl nitrite (60 mmol) is added dropwise over thirty minutes (30 min) and the mixture is stirred for 18–24 hours at 120°–130° C. The excess phenol is removed by evaporation and the intermediate product is recovered on a silica gel column using an appropriate solvent such as petroleum spirit/acetone (9/1, v/v). The solvent is evaporated and the residue is dissolved in an appropriate diluent such as dimethyl sulfoxide or hexamethylphosphoramide (HMPA). Anhydrous potassium carbonate (60 mmol) (or another appropriate base such as sodium carbonate) is added and the mixture is stirred for 1 to 2 hours at 180°–200° C. The substituted dibenzofuran is recovered from a silica gel column and is recrystallized in an appropriate solvent such as anisole/methanol (1/9, v/v) or chloroform/methanol (1/9, v/v). A single or repeated (2×) recrystallization gives the pure product (>98% as determined by gas chromatography). Farrell, K., et al., Arch. Blochem. Biophys. 259:185–195 (1987) and Mason, G., et al., Toxicology 37:1–12 (1985).

In the alterative synthetic pathway, the substituted aminoanisole (20 mmol) and chlorinated or halogenated benzene (100 mmol) are heated and mixed with stirring at 120°–130° C. Isoamyl nitrite (60 mmol) is added dropwise over 30 minutes and the reaction mixture is stirred for 18–24 hours at 120°–130° C. The excess chlorinated benzene is removed by evaporation and the intermediate product is recovered on a silica gel column using an appropriate solvent such as petroleum spirit. The solvent is evaporated and the substituted methoxybiphenyl is dissolved in methylene chloride and treated with excess boron tribromide (100–200 mmol) in methylene chloride. The rate of demethylation is monitored by gas liquid or thin-layer chromatography and, after demethylation has occurred, the reaction is terminated by the careful addition of water and the substituted hydroxybiphenyl is subsequently isolated in the methylene chloride fraction. The solvent is removed and dissolved in an appropriate diluent such as dimethyl sulfoxide (DMSO) or hexamethylphosphoramide (HMPA). Anhydrous potassium carbonate (60 mmol) (or another appropriate base such as sodium carbonate) is added and the mixture is stirred for 1–2 hours at 180°–200° C. The substituted dibenzofuran is recovered from a silica gel column and is recrystallized in an appropriate solvent such as anisole/methanol (1/9, v/v) or chloroform/methanol (1/9, v/v). A single or repeated (2×) recrystallization gives the pure product (>98% as determined by gas chromatography) using the technique of Farrell, K., et al., Arch. Blochem. Biophys. 259:185–195 (1987) and Mason, G., et al., Toxicology 37:1–12 (1985).

Synthesis of 1,3,6,8 and 2,4,6,8 Substituted Dibenzofurans

The starting reactants for 1,3,6,8 and 2,4,6,8-substituted dibenzofuran are substituted phenols and substituted 6-haloanilines. The composition of the substituted dibenzofuran end product is dependent upon the positions of the substituents on the substituted phenol and the substituted haloaniline. Because the substituted dibenzofuran is symmetrical through the vertical axis, the end product and the beginning reactants could be renamed for their mirror images. To be consistent, this discussion will discuss the reactants and the end product as pictured in diagram 2

Diagram 2

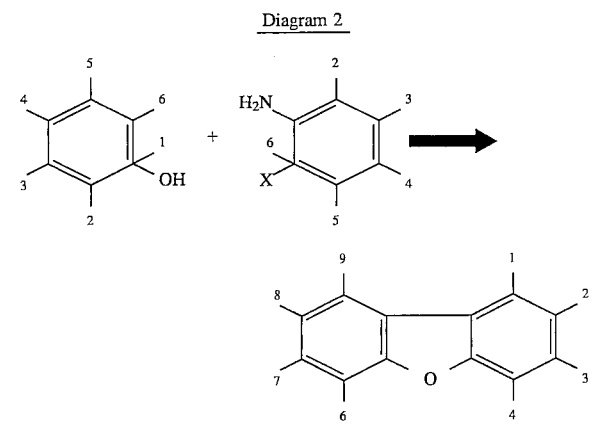

where X is a halogen.

Possible substituents are halogens and/or linear or branched substituents such as alkyl groups of about one to about four carbons. The carbon positions may also be individually and independently occupied by a hydrogen instead of a substituent. In the preferred mode, the halogen substituents will be chlorine or bromine, the alkyl will be of about one to about four carbon atoms, and the substituents of the reactants will be such that the final substituted dibenzofuran will be substituted with an alkyl group at position 6. Suitable alkyl substituents include, but are not limited to, methyl, ethyl, propyl, iso-propyl (i-propyl), n-butyl, sec-butyl or tert-butyl groups. In addition, no more than one of the positions of the end product which could be occupied by a substituent or a hydrogen should be occupied by a hydrogen and at least two of the positions should be occupied by halogen substituents.

The substituted phenol (100 mmol) and substituted 6-haloaniline (20 mmol) are mixed and heated with stirring at 120°–130° C. Isoamyl nitrite (60 mmol) is added dropwise over thirty minutes (30 min) and the mixture is stirred for 18–24 hours at 120°–130° C. The excess phenol is removed by evaporation and the intermediate product is recovered on a silica gel column using an appropriate solvent such as petroleum spirit/acetone (9/1, v/v). The solvent is evaporated and the residue is dissolved in an appropriate diluent such as dimethyl sulfoxide or hexamethylphosphoramide (HMPA). Anhydrous potassium carbonate (60 mmol) (or another appropriate base such as sodium carbonate) is added and the mixture is stirred for 1 to 2 hours at 180°–200° C. The substituted dibenzofuran is recovered from a silica gel column and is recrystallized in an appropriate solvent such as anisole/methanol (1/9, v/v) or chloroform/methanol (1/9, v/v). A single or repeated (2×) recrystallization gives the pure product (>98% as determined by gas chromatography) using the technique of Farrell, K., et al., Arch. Biochem. Biophys. 259:185–195 (1987) and Mason, G., et al., Toxicology 37:1–12 (1985).

Synthesis of 1,3,6,8 or 2,4,6,8-Substituted Dibenzo-p-Dioxin

Two different methods for the synthesis of 1,3,6,8 or 2,4,6,8-substituted dibenzo-p-dioxins will be discussed. As with the dibenzofurans the appropriate substituted dibenzo-p-dioxins are obtained by the positioning of the appropriate substituents on the reactants or starting materials. Because the dibenzo-p-dioxin is symmetrical on two axes the beginning reactants and the final product could be characterized in many different ways. For the sake of consistency all of the reactants and the final product will be named as depicted in diagrams 3 and 4.

Diagram 3

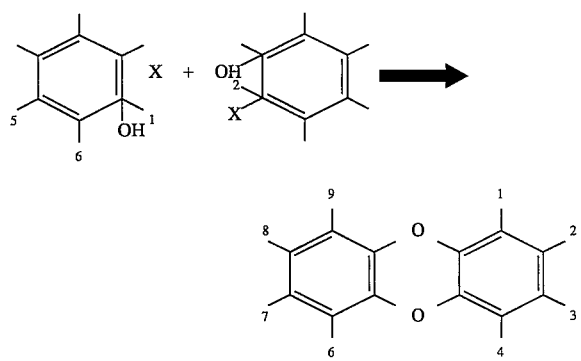

where X is a halogen.

Diagram 4

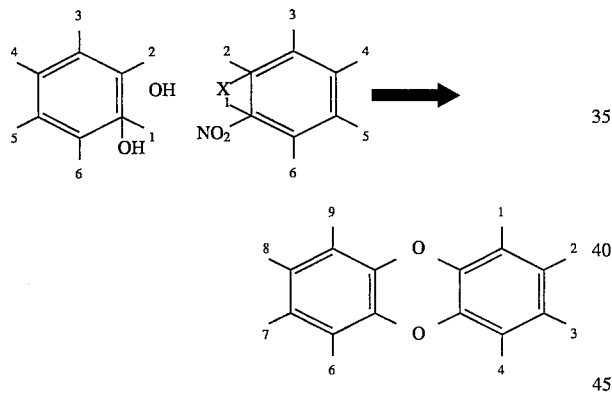

where X is a halogen.

Possible substituents are halogens and/or linear or branched substituents such as alkyl groups of about one to about four carbons. Halogens include chlorine, fluorine, and bromine. The carbon positions may also be independently and individually occupied by a hydrogen instead of a substituent. In the preferred mode, the halogen substituents will be chlorine or bromine, the alkyl will be of about one to about four carbon atoms, and the substituents on the reactants will be such that the final substituted dibenzo-p-dioxin will be substituted with an alkyl group at position six. Suitable alkyl substituents include, but are not limited to, methyl, ethyl, propyl, iso-propyl (i-propyl), n-butyl, sec-butyl or tert-butyl groups. In addition, no more than one of the positions of the end product which may be filled by either a substituent or a hydrogen will be occupied by a hydrogen and at least two of the substituents will be halogens.

The preferred method of synthesis utilizes 2,4,6-substituted phenols as the starting reactants. The sodium salt of the appropriately substituted phenols in the presence of an appropriate diluent such as dimethyl sulfoxide are heated at 220°–250° for 16–24 hours. The mixture is adsorbed on silicic acid and is recovered on a silica gel column using an appropriate solvent such as petroleum spirit. The solvent is removed and the residue is recrystallized from an appropriate solvent such as anisole/methanol (1/9, v/v) or chloroform/methanol (1/9, v/v) yielding 1,3,6,8-substituted dibenzo-p-dioxins. The minor product 1,3,7,9-substituted dibenzo-p-dioxin (2,4,6,8-tetrachlorodibenzo-p-dioxin) can be recovered from the mother liquors and further purified by high pressure liquid chromatography.

Another method which may be used for synthesis of 1,3,6,8 or 2,4,6,8-substituted dibenzo-p-dioxins utilizes a substituted catechol and a substituted halonitrobenzene as the starting reactants. The substituted catechol (3 mmol) and the substituted halonitrobenzene (3 mmol) and anhydrous potassium carbonate (12 mmol) (or another appropriate base) and an appropriate diluent such as dimethyl sulfoxide or HMPA are heated with stirring at 180°–190° C. for 1–4 hours. The mixture is adsorbed on silicic acid and is recovered on a silica gel column using an appropriate solvent such as petroleum spirit or hexane. The solvent is removed and the residue is recrystallized from an appropriate solvent such as anisole/methanol (1/9, v/v) or chloroform/methanol (1/9, v/v).

Antiestrogenic Effects of Alkyl-Substituted Dibenzofurans

The alkyl substituted dibenzofurans synthesized above may be used as antiestrogens. MDCF has been utilized as a prototype for investigating the antiestrogenic activities of the 6-alkyl-substituted-1,3,8-trichlorodibenzofurans and it is clear that this compound inhibits a broad spectrum of $17\beta$-estradiol-induced responses which include:

(1) the upregulation of uterine nuclear and cytosolic estrogen and progesterone receptor levels (Astroff and Safe, *Toxicol. Appl. Pharmacol.*, 95:435–443, 1988).

(2) uterotrophic effects (Astroff and Safe, *Biochem. Pharmacol.*, 39:485–488, 1990)

(3) increased EGF receptor binding and mRNA levels (manuscript submitted), (4) the growth of MCF-7 cells (Biegel, Ph.D. Dissertation, Texas A&M University, 1990), (5) the accumulation of nuclear ER levels in MCF-7 cells (Harris et al., Cancer Res., 50:3579–3584, 1990), and (6) the secretion of the 34-, 52- and 160-kDa proteins in MCF-7 cells (Biegel and Safe, *J. Ster. Biochem.*, 37: 725–32 (1990 ) ).

MCDF when administered with $17\beta$-estradiol will significantly reduce or inhibit $17\beta$-estradiol-mediated responses. In comparison to control test animals, MCDF decreases the nuclear and cytosolic hepatic and uterine estrogen receptor levels and decreases uterine wet weights in rats and mice. These effects can be observed using amounts of MCDF which are nontoxic. A detailed description of the antiestrogenic effects of MCDF has been reported. Toxicol. Appl. Pharmacol. 95:435–443 (1988). Results have also been obtained which show that these compounds will be useful as antiestrogens in human breast cancer cells. Zacharewski, et al., Toxicol. Appl. Pharmacol. 113:311–318 (1992) (Example 9). In addition the effects of several other 1,3,6,8-substituted dibenzofurans (i.e., 2-lateral substituents) in the female rat uterus are summarized in Table 1.

It appears that the antiestrogenic effects of the alkylated dibenzofurans are somehow related to the ability of these compounds to bind to the Ah receptor. It is this binding activity which also allows these compounds to antagonize 2,3,7,8-tetrachlorodibenzo-p-dioxin-mediated induction of aryl hydrocarbon hydroxylase (AHH), other monooxygenase enzymes, and other toxic responses. The alkyl-substituted dibenzofurans which contain either 3 or 4 lateral substituents will act in the same fashion due to their structural similarity and exhibit equally low toxicity.

The preferred mode for use of these compounds as an antiestrogenic compound and for treatment of estrogen-dependent tumors is the administration of an alkyl-substituted dibenzofuran with the substituent being a linear or branched alkyl group of about one to about four carbons. This compound should be administered in a biologically active amount dissolved in a carrier suitable for lipid soluble compounds such as corn oil or soybean oil. An aqueous emulsion or encapsulation could also be used to administer the drug orally.

Antiestrogenic Effects of 1,3,6,8 and 2,4,6,8-Substituted Dibenzofurans and Dibenzo-p-Dioxins The 1,3,6,8 and 2,4,6,8-substituted dibenzofurans and dibenzo-p-dioxins synthesized as described above may be used as antiestrogens. MCDF when administered with estradiol will significantly reduce or inhibit 17β-estradiol mediated responses. In comparison to control test animals, MCDF decreases the number of nuclear and cytosolic hepatic and uterine estrogen receptors and decreases uterine wet weights in rats and mice. These effects can be observed using amounts of MCDF which are nontoxic. A detailed description of the antiestrogen effect of MCDF is given in example 3. Results have also been obtained which suggest these compounds will be useful as antiestrogens in human breast cancer cells (See example 5).

While it is unclear by what mechanism the 1,3,6,8 substituted dibenzofurans act, it appears that the antiestrogenic effect is somehow related to the ability of these compounds to bind to the Ah receptor. It is this binding activity which also allows these compounds to act as antagonists to 2,3,7,8-tetrachlorodibenzo-p-dioxin in its effects as an inducer of aryl hydrocarbon hydroxylase (AHH), other monooxygenase enzymes, and other toxic responses (Keys et al., Toxicol. Letters 31:151–158 (1986) and Banister et al., Chemosphere, Volume 16 Nos. 8/9 pages 1739–1742, 1987). The 2,4,6,8-substituted dibenzofurans and the 1,3,6,8 and 2,4,6,8-substituted dibenzo-p-dioxins will act in the same fashion due to their structural similarity and exhibit equally low toxicity.

The preferred mode for use of these compounds as an antiestrogenic and for treatment of estrogen dependent tumors is the administration of a 6-substituted 1,3,8-trichlorodibenzofuran or dibenzo-p-dioxin with the substituent at position 6 being a linear or branched alkyl group of one to four carbons. This compound should be administered in a biologically active amount, which in test animals is 50–100 µg/kg, dissolved in a carrier suitable for lipid soluble compounds such as corn oil or soybean oil. An aqueous emulsion or encapsulation could also be used to administer the drug orally.

The following examples serve to illustrate specific embodiments of this invention, but should not be considered as limiting the scope of the invention.

EXAMPLE 1

Synthesis of a 6-methyl or 6-alkyl-substituted dibenzofuran which contains 3 lateral substituents.

2-Methyl-4-chlorophenol (20 gms) (Aldrich Chemicals) and 2,3,4,5-tetrachloroaniline (5 gms) (Aldrich Chemicals) were mixed and heated with stirring to 120° C. Isoamyl nitrite (6 mls) was added dropwise over a 30-min period and the mixture was stirred for 18 h at 120° C. The excess phenol was removed by evaporation and the residue was adsorbed on silica gel and added to the top of a silica gel column packed with petroleum spirit/acetone (9/1, v/v). The column was eluted with 500 ml of the above solvent, the solvent was evaporated, and the residue was dissolved in dimethyl sulfoxide. Anhydrous potassium carbonate (500 mg) was added and the mixture was stirred for 2 h at 190° C. The mixture was then adsorbed on 30–40 gms of silica gel, the solvent was evaporated and the silica gel was added to the top of a 20×5 cm silica gel column which was packed and equilibrated with petroleum spirit. 6-Methyl-2,3,4,8-tetrachlorodibenzofuran was eluted from the column with 500 ml of petroleum spirit and the residue was crystallized from anisole/methanol (1/9, v/v). The amount of product recovered was 320 mg and was >98% pure as determined by gas chromatographic analysis and a molecular weight confirmation with a VG 12000 quadrupole mass chromatograph coupled to a Hewlett Packard 500 gas chromatograph.

EXAMPLE 2

Synthesis of an 8-methyl or 8-alkyl-substituted dibenzofuran which contains 3 lateral substituents.

1,3,5-Trichlorobenzene (20 gms) (Aldrich Chemicals) and 4-chloro-5-methyl-o-anisidine (5 gms) (Aldrich Chemicals) were mixed and heated with stirring to 120° C. Isoamyl nitrite (6 mls) was added dropwise over a 30-min period and the mixture was stirred for 18 h at 120° C. The excess chlorinated benzene was removed by evaporation and the residue was adsorbed on silica gel and added to the top of a silica gel column packed with petroleum spirit. The column was eluted with 500 ml of the above solvent, the solvent was evaporated, and the residue was dissolved in methylene chloride and treated with a 5- to 10-fold molar excess of boron tribromide in methylene chloride. The reaction was monitored by gas and thin-layer chromatography and, when demethylation was complete (2 to 3 days), the reaction was terminated by the careful addition of 10 ml of water. The product was isolated by extraction with methylene chloride. The dried extract was evaporated to dryness and the residue dissolved in 5 ml DMSO and anhydrous potassium carbonate (500 mg) was added and the mixture was stirred for 2 h at 190° C. The reaction mixture was then adsorbed on 30–40 gms of silica gel. The solvent was evaporated and the silica gel was added to the top of a 20×5 cm silica gel column which was packed and equilibrated with petroleum spirit. 8-Methyl-1,3,7-trichlorodibenzofuran was eluted from the column with 500 ml of petroleum spirit and the residue was crystallized from anisole/methanol (1/9, v/v). The amount of product recovered was 250 mg and was 97% pure as determined by gas chromatographic analysis and a molecular weight confirmation with a VG 12000 quadrupole mass chromatograph coupled to a Hewlett Packard 500 gas chromatograph.

EXAMPLE 3

Synthesis of alkyl-substituted dibenzofurans with 4 lateral substituents.

3-Methyl-4-chlorophenol (20 gms) (Aldrich Chemicals) and 2,4,5-trichloroaniline (5 gms) (Aldrich Chemicals) were mixed and heated with stirring to 120° C. Isoamyl nitrite (6 ml) was added dropwise over a 30-min period and the mixture was stirred for 18 h at 120° C. The excess phenol was removed by evaporation and the residue was adsorbed on silica gel and added to the top of a silica gel column packed with petroleum spirit/ acetone (9/1, v/v). The column was eluted with 500 ml of the above solvent, the solvent was evaporated, and the residue was dissolved in dimethyl sulfoxide. Anhydrous potassium carbonate (500 mg) was added and the mixture was stirred for 2 h at 190° C. It was then adsorbed on 30–40 gms of silica gel. The solvent was evaporated and the silica gel was added to the top of a 20×5 cm silica gel column which was packed and equilibrated with petroleum spirit. The 7-methyl-2,3,8-trichlorodibenzofuran (plus the 1-methyl-2,7,8-trichlorodibenzofuran by-product) was eluted from the column with 500 ml of petroleum spirit and the residue was crystallized from anisole/methanol (1/9, v/v). The amount of product recovered was 300 mg and eluted as a single peak (determined by gas chromatographic analysis) and a molecular weight confirmation with a VG 12000 quadrupole mass chromatograph coupled to a Hewlett Packard 500 gas chromatograph.

EXAMPLE 4

Synthesis of an 8-methyl or 8-alkyl-substituted dibenzofuran which contains 4 lateral substituents.

1,2,3,4-Tetrachlorobenzene (20 gms) (Aldrich Chemicals) and 4-chloro-5-methyl-o-anisidine (5 gms) (Aldrich Chemicals) were mixed and heated with stirring to 120° C. Isoamyl nitrite (6 mls) was added dropwise over a 30-min period and the mixture was stirred for 18 h at 120° C. The excess chlorinated benzene was removed by evaporation and the residue was adsorbed on silica gel and added to the top of a silica gel column packed with petroleum spirit. The column was eluted with 500 ml of the above solvent, the solvent was evaporated, and the residue was dissolved in methylene chloride and treated with a 5- to 10-fold molar excess of boron tribromide in methylene chloride. The reaction was monitored by gas and thin-layer chromatography and when demethylation was complete (2 to 3 days), the reaction was terminated by the careful addition of 10 ml of water. The product was isolated by extraction with methylene chloride. The dried extract was evaporated to dryness and the residue dissolved in 5 ml DMSO and anhydrous potassium carbonate (500 mg) was added and the mixture was stirred for 2 h at 190° C. It was then adsorbed on 30–40 gms of silica gel. The solvent was evaporated and the silica gel was added to the top of a 20×5 cm silica gel column which was packed and equilibrated with petroleum spirit. 8-Methyl-2,3,4,7-tetrachlorodibenzofuran was eluted from the column with 500 ml of petroleum spirit and the residue was crystallized from anisole/methanol (1/9, v/v). The amount of product recovered was 285 mg and was 97% pure as determined by gas chromatographic analysis and a molecular weight confirmation with a VG 12000 quadrupole mass chromatograph coupled to a Hewlett Packard 500 gas chromatograph.

EXAMPLE 5

Synthesis of 6-methyl 1,3,8-trichlorodibenzofuran.

20 gms. of 2-methyl-4-chlorophenol (Aldrich Chemicals) and 5 gms. of 2,4,6-trichloroaniline (Aldrich Chemicals) were mixed and heated with stirring to 120° C. 6 mls. of isoamyl nitrate was added dropwise over a thirty minute period and the mixture was stirred for 18 hours at 120° C. The excess phenol was removed by evaporation and the residue was adsorbed on silica gel and added to the top of a silica gel column packed with petroleum spirit/diethylether (3:7). The column was eluted with 500 ml. of the above solvent, the solvent was evaporated, and the residue was dissolved in dimethyl sulfoxide. 500 mg. of anhydrous potassium carbonate was added and the mixture was stirred for two hours at 190° C. It was then adsorbed on 30–40 grams of silica gel. The solvent was evaporated and the silica gel was added to the top of a 20×5 cm silica gel column which was packed and equilibrated with petroleum spirit. 6-methyl 1,3,8-trichlorodibenzofuran was eluted from the column with 500 mls. of petroleum spirit and the residue was crystallized from anisole/methanol (1:9). 280 mgs. of the product was recovered and was 99% pure as determined by gas chromatographic analysis and a molecular weight of 284 was confirmed with a VG 12000 quadrupole mass chromatograph coupled to a Hewlett Packard 500 gas chromatograph. The 220-MHz. proton magnetic resonance spectrum (in deuterochloroform) was determined with a Varian XL200 spectrometer and gave (in $CDCL_3$): 8.07 (H-9,d,J= 1.6 Hz) 7.48, 7.33 (H-1/H-3, d,J=1.6 Hz); 7.29, 7.29ppm (H-7,m).

EXAMPLE 6

Synthesis of 1,3,6,8-tetrachlorodibenzo-p-dioxin.

This is a prophetic example. 2.5 gms. of the sodium salt of 2,4,6-trichlorophenol and 5 to 7 mls. of dimethylsulfoxide are stirred at 200–200° C. for 16–24 hours. The reaction mixture is adsorbed on 10 gms. of silica gel, the solvent is allowed to evaporate and the absorbed reaction mixture is placed on top of a silica gel column (60 gms. silica gel, 4×2 mm). The column is eluted with 500 mls. of petroleum spirit. The solvent is removed in vacuo and the residue is recrystallized from 4 mls. of anisole/methanol (1:9) to give a 1–10% yield of 1,3,6,8-tetrachlorodibenzo-p-dioxin. The minor product 1,3,7,9-tetrachlorodibenzo-p-dioxin (2,4,6,8-tetrachlorodibenzo-p-dioxin) can be recovered from the mother liquors and further purified by high pressure liquid chromatography or by recrystallization from anisole/methanol.

EXAMPLE 7

Synthesis of 6-methyl 1,3,8-trichlorodibenzo-p-dioxin.

This is a prophetic example. 480 mg. of 6-methyl-4-chloro-catechol, 680 mg. of 2,3,5-(or 2,4,6) trichloronitrobenzene, 420 mg. of anhydrous potassium carbonate and 3 mls. of dimethyl sulfoxide are heated with stirring at 180° C. for four hours. The mixture is adsorbed on 30 gms. of silicic acid, the solvent is allowed to evaporate, and the material is placed as a top layer on a 20×5 cm silica gel column (60 gms. of silicic gel packed with petroleum spirit). The material is eluted with 350 ml. of petroleum spirit. The solvent is removed in vacuo and the residue is recrystallized from 4 ml. of anisole/methanol (1/9 v/v). The crystals are removed by filtration to give 0.15 gms. of 6-methyl 1,3,8-trichlorodibenzo-p-dioxin. This compound may also contain 9-methyl-1,3,7-trichlorodibenzo-p-dioxin as an impurity. This compound is expected to exhibit comparable activity due to the 2-fold axis of symmetry of this molecule.

EXAMPLE 8

Antiestrogenic activities of alkyl-substituted dibenzofurans.

Twenty-five day old female Sprague-Dawley rats, at least four rats in each treatment group, were injected with either corn oil (control), 17β-estradiol (5 μmol/rat, sid×2 days), TCDD, alkyl-substituted dibenzofurans, 17β-estradiol plus TCDD or 17β-estradiol plus alkyl-substituted dibenzofurans (see Tables 4–6 for dose levels). TCDD or the alkyl-substituted dibenzofurans were co-administered with a second dose of 17β-estradiol and the animals were killed 48 hours later. A second group of animals was similarly treated with corn oil, TCDD, MCDF, or TCDD plus MCDF, all administered in corn oil at 10 ml/kg and terminated 72 hours later.

The animals were terminated by cervical dislocation. Livers were perfused with ice-cold TEDG buffer (10 mM Tris-HCl, 1.5 mM EDTA-4Na, 1 mM dithiothreitol, 10% glycerol (v/v), pH 7.4). Following perfusion in situ, livers were removed, weighed, and homogenized in ice-cold TEDG buffer. Uteri were also removed, weighed, and homogenized in ice-cold buffer. The homogenates were then centrifuged at 800×g (200 rpm) for 15 minutes and the nuclear pellets were stored at −80° C. The supernatants were further centrifuged at 180,000× g for 1.5 hours. The cytosolic supernatant was also stored at −80° C. Estrogen and progesterone receptor levels were determined within 7 days.

Estrogen (ER) and progesterone (PR) receptor levels were determined by the hydroxyapatite assay as described by Clark et al. (*J. Steroid Biochem.* 16:323–328, 1982) and incorporated herein by reference. Briefly, samples were incubated with 10 nM [$^3$H]-17β-estradiol or the progesterone analog [$^3$H]-R5020 (New England Nuclear—Boston, Mass., USA) with or without 200-fold excess cold diethylstilbestrol (DES) or progesterone, respectively. Following the incubations, samples were counted and specific binding was calculated by subtraction of nonspecific from total binding. Assuming one steroid molecule binds to one estrogen/progesterone receptor, the number of moles of receptor can be calculated given the specific activity of the radioligand. The data presented in Tables 1 through 6 are means ± SD using at least four animals per treatment group. Significant differences were determined by analysis of variance.

The results of these experiments are shown in the following Tables.

The results in Table 1 summarize the effects of MCDF and several alkyl 1,3,6,8-substituted dibenzofurans (at a dose of 150 μmol/kg) as antiestrogens in the female rat uterus. All of these compounds significantly inhibited the 17β-estradiol-induced increases in uterine wet weights and in uterine ER and PR levels.

TABLE 1

Antiestrogenic Effects of 1,3,6,8-Substituted Dibenzofurans in Immature Female Sprague-Dawley Rats (150 μmol/kg) (2 lateral substituents).

| Compound | Uterine Wet Weight (% body wt) | Estrogen Receptor Levels (fmol/mg protein) | | Progesterone Receptor Levels (fmol/mg protein) | |
|---|---|---|---|---|---|
| | | Cytosolic | Nuclear | Cytosolic | Nuclear |
| A* | | | | | |
| Corn oil | 0.128 ± 0.010 | 82.1 ± 3.2 | 53.3 ± 1.5 | 1160 ± 31 | 510 ± 63 |
| 17β-Estradiol (E-2) | 0.265 ± 0.026 | 152.7 ± 1.1 | 79.3 ± 72.5 | 2590 ± 45 | 810 ± 75 |
| MCDF | 0.104 ± 0.004 | 55.1 ± 0.9 | 49.3 ± 10.2 | 915 ± 63 | 312 ± 50 |
| + 3-2 | 0.194 ± 0.023 | 78.9 ± 79.1 | 43.3 ± 73.4 | 1203 ± 110 | 435 ± 91 |
| 8-Methyl-1,3,6-triCDF | 0.089 ± 0.008 | 54.1 ± 6.2 | 38.1 ± 5.8 | 686 ± 77 | 188 ± 29 |
| + E-2 | 0.212 ± 0.021 | 65.9 ± 77.5 | 20.8 ± 70.5 | 838 ± 66 | 203 ± 35 |
| 1,3,6,8-tetraCDF | 0.123 ± 0.004 | 55.2 ± 5.6 | 18.5 ± 3.5 | 571 ± 49 | 199 ± 46 |
| + E-2 | 0.187 ± 0.020 | 75.5 ± 17.3 | 16.1 ± 2.3 | 798 ± 83 | 291 ± 71 |
| B* | | | | | |
| Corn oil | 0.103 ± 0.011 | 106.0 ± 3.8 | 42.3 ± 2.1 | 891 ± 54 | 394 ± 28 |
| 17β-Estradiol (E-2) | 0.321 ± 0.019 | 188.7 ± 74.0 | 75.5 ± 3.8 | 2233 ± 128 | 1142 ± 80 |
| 6-Ethyl-1,3,8-triCDF | 0.128 ± 0.007 | 98.4 ± 5.5 | 33.9 ± 1.7 | 688 ± 49 | 243 ± 17 |
| + E-2 | 0.226 ± 0.013 | 104.3 ± 77.1 | 34.9 ± 1.8 | 1601 ± 121 | 277 ± 19 |
| 6-n-Propyl-1,3,8-triCDF | 0.118 ± 0.008 | 86.4 ± 8.1 | 35.4 ± 1.8 | 740 ± 71 | 294 ± 21 |
| + E-2 | 0.240 ± 0.019 | 169.4 ± 6.0 | 33.7 ± 1.7 | 1838 ± 62 | 408 ± 29 |
| 6-i-Propyl-1,3,8-triCDF | 0.154 ± 0.017 | 95.2 ± 6.2 | 57.7 ± 2.9 | 1225 ± 59 | 242 ± 17 |
| + E-2 | 0.210 ± 0.012 | 135.5 ± 78.1 | 52.6 ± 2.6 | 2131 ± 76 | 272 ± 19 |
| 6-t-Butyl-1,3,8-triCDF | 0.122 ± 0.013 | 85.5 ± 4.3 | 41.4 ± 2.1 | 1109 ± 83 | 211 ± 15 |
| + B-2 | 0.247 ± 0.004 | 108.6 ± 11.4 | 41.7 ± 2.1 | 1844 ± 77 | 270 ± 19 |

*Two different runs; the dose of 17β-estradiol was 2 × 10 μg/rat.

The results in Table 2 summarize the antiestrogenic activity of a series of alkyl-substituted dibenzofurans which contain 3 lateral substituents. These compounds include 6-methyl-2,3,8-trichloro-, 6-methyl-2,3,4,8-tetrachloro-, and 8-methyl-1,3,7-trichloro- and 8-methyl-1,2,4,7-tetrachlorodibenzofuran. All of these congeners exhibited antiestrogenic effects at a dose of 50 μmol/kg and there were decreases in 17β-estradiol-induced uterine wet weights and uterine ER and PR levels.

TABLE 2

Antiestrogenic Effects of Alkyl-Substituted Dibenzofurans in Immature Female Sprague-Dawley Rats (50 μmol/kg) (3 lateral substituents).

| Compound | Uterine Wet Weight (% body wt) | Estrogen Receptor Levels (fmol/mg protein) | | Progesterone Receptor Levels (fmol/mg protein) | |
|---|---|---|---|---|---|
| | | Cytosolic | Nuclear | Cytosolic | Nuclear |
| Corn oil | 0.108 ± 0.015 | 107.0 ± 11.1 | 59.5 ± 61.3 | 1110 ± 99 | 624 ± 56 |
| 17β-Estradiol (E-2)* | 0.297 ± 0.031 | 168.7 ± 19.3 | 129.5 ± 15.0 | 2938 ± 302 | 1143 ± 112 |
| 6-Methyl-2,3,8-triCDF | 0.125 ± 0.024 | 84.3 ± 9.3 | 55.8 ± 7.1 | 356 ± 65 | 395 ± 52 |
| + E-2 | 0.204 ± 0.020 | 105.3 ± 12.2 | 70.8 ± 8.1 | 1062 ± 121 | 622 ± 71 |
| 6-Methyl-2,3,4,8-tetraCDF | 0.109 ± 0.020 | 96.2 ± 11.2 | 31.3 ± 5.6 | 625 ± 71 | 457 ± 58 |
| + E-2 | 0.163 ± 0.019 | 176.3 ± 20.3 | 69.9 ± 9.4 | 795 ± 52 | 1081 ± 131 |
| 8-Methyl-1,3,7-triCDF | 0.127 ± 0.019 | 72.8 ± 8.3 | 26.4 ± 5.1 | 503 ± 63 | 795 ± 92 |
| + E-2 | 0.181 ± 0.007 | 119.0 ± 14.3 | 51.1 ± 7.4 | 1025 ± 151 | 952 ± 113 |
| 8-Methyl-1,2,4,7-tetraCDF | 0.175 ± 0.007 | 97.1 ± 10.1 | 40.6 ± 5.3 | 685 ± 59 | 303 ± 46 |
| + E-2 | 0.213 ± 0.017 | 118.4 ± 14.6 | 66.5 ± 8.9 | 841 ± 73 | 399 ± 75 |

*The dose of 17β-estradiol was 2 × 10 μg/rat.

Table 3 summarizes the same set of antiestrogenic responses in female Sprague-Dawley rats which were elicited by a series of alkyl-substituted dibenzofurans which contained 3 lateral substituents (at a dose of 50 μmol/kg). The compounds used in this study included 8-methyl-2,3,7-trichloro-, 8-methyl-2,3,7-dibromo-, (triBDD) 8-methyl-2,3,4,7-tetrachloro- and 7-methyl-2,3,8-trichlorodibenzofuran.

In addition, the relative dose-response antiestrogenic potencies of selected alkyl-substituted dibenzofurans which contain 2, 3 or 4 lateral substituents were also determined in the female Sprague-Dawley rats (Tables 4 through 6). The results of these studies clearly showed that the antiestrogenic potencies of the alkyl-substituted dibenzofurans were dependent for most of the responses on the number of lateral substituents (Table 7) and the relative potencies (i.e., decreasing EC50 values) increased with increasing lateral substituents.

TABLE 3

Antiestrogenic Effects of Alkyl-Substituted Dibenzofurans in Immature Female Sprague-Dawley Rats (50 μmol/kg) (4 lateral substituents).

| Compound | Uterine Wet Weight (% body wt) | Estrogen Receptor Levels (fmol/mg protein) | | Progesterone Receptor Levels (fmol/mg protein) | |
|---|---|---|---|---|---|
| | | Cytosolic | Nuclear | Cytosolic | Nuclear |
| Corn oil | 0.124 ± 0.007 | 113.6 ± 5.7 | 43.9 ± 2.2 | 934 ± 56 | 415 ± 25 |
| 17β-Estradiol (E-2)* | 0.363 ± 0.032 | 209.4 ± 1.1 | 65.4 ± 3.3 | 2380 ± 143 | 1246 ± 75 |
| 8-Methyl-2,3,7-triCDD | 0.138 ± 0.026 | 113.9 ± 5.7 | 47.8 ± 2.4 | 554 ± 33 | 177 ± 11 |
| + E-2 | 0.237 ± 0.007 | 85.7 ± 4.3 | 25.7 ± 1.3 | 607 ± 36 | 204 ± 12 |
| 8-Methyl-2,3,7-triBDD | 0.153 ± 0.003 | 128.2 ± 7.7 | 64.3 ± 4.6 | 362 ± 22 | 270 ± 16 |
| + E-2 | 0.259 ± 0.020 | 133.3 ± 6.7 | 80.0 ± 4.8 | 505 ± 35 | 221 ± 15 |
| 8-Methyl-2,3,4,7-tetraCDF | 0.094 ± 0.006 | 66.8 ± 3.3 | 30.9 ± 1.6 | 616 ± 43 | 161 ± 13 |
| + E-2 | 0.245 ± 0.006 | 107.2 ± 5.4 | 43.7 ± 2.2 | 725 ± 51 | 360 ± 25 |
| 7-Methyl-2,3,-triCDF | 0.102 ± 0.011 | 72.9 ± 3.7 | 35.2 ± 1.8 | 501 ± 35 | 364 ± 26 |
| + E-2 | 0.255 ± 0.017 | 94.2 ± 4.71 | 48.1 ± 2.4 | 924 ± 74 | 554 ± 39 |

*The dose of 17β-estradiol was 2 × 10 μg/rat.

TABLE 4

Dose-Response Antiestrogenic Effects of 6-Propyl-1,3,8-Trichlorodibenzofuran in Immature Female Sprague-Dawley Rats (2 lateral substituents).

| Dose* (μmol/kg) | Uterine Wet Weight (% body wt) | Estrogen Receptor Levels (fmol/mg protein) | | Progesterone Receptor Levels (fmol/mg protein) | |
|---|---|---|---|---|---|
| | | Cytosolic | Nuclear | Cytosolic | Nuclear |
| 10 | 0.192 ± 0.013 | 105.5 ± 5.3 | 81.5 ± 4.9 | 1501 ± 105 | 850 ± 68 |
| 25 | 0.170 ± 0.010 | 87.8 ± 4.4 | 56.6 ± 2.8 | 1055 ± 74 | 515 ± 41 |
| 50 | 0.202 ± 0.014 | 66.7 ± 3.3 | 41.1 ± 2.1 | 1105 ± 77 | 510 ± 41 |
| 150 | 0.216 ± 0.012 | 88.2 ± 4.4 | 35.6 ± 1.8 | 1190 ± 83 | 660 ± 53 |
| E-2 | 0.283 ± 0.013 | 172.8 ± 8.6 | 82.7 ± 5.0 | 1635 ± 115 | 935 ± 75 |

*Each dose of compound was accompanied by cotreatment with 17β-estradiol (2 × 10 μg/rat).

TABLE 5

Dose-Response Antiestrogenic Effects of 6-Methyl-2,3,4,8-Tetrachlorodibenzofuran in Immature Female Sprague-Dawley Rats (3 lateral substituents).

| Dose* (μmol/kg) | Uterine Wet Weight (% body wt) | Estrogen Receptor Levels (fmol/mg protein) | | Progesterone Receptor Levels (fmol/mg protein) | |
|---|---|---|---|---|---|
| | | Cytosolic | Nuclear | Cytosolic | Nuclear |
| 2 | 0.268 ± 0.044 | 86.7 ± 4.3 | 64.7 ± 3.9 | 1220 ± 85 | 925 ± 74 |
| 10 | 0.221 ± 0.020 | 83.9 ± 4.2 | 53.8 ± 3.2 | 970 ± 68 | 765 ± 61 |
| 25 | 0.191 ± 0.006 | 75.1 ± 3.8 | 49.3 ± 3.0 | 1000 ± 63 | 645 ± 52 |
| 50 | 0.158 ± 0.004 | 71.0 ± 3.6 | 40.0 ± 2.4 | 885 ± 53 | 450 ± 36 |
| E-2 | 0.283 ± 0.013 | 172.8 ± 8.6 | 82.7 ± 5.0 | 1635 ± 116 | 935 ± 75 |

*Each dose of compound was accompanied by cotreatment with 17β-estradiol (2 × 10 μg/rat).

TABLE 6

Dose-Response Antiestrogenic Effects of 8-Methyl-2,3,7-Trichlorodibenzofuran (A) and 8-Methyl-2,3,4,7-Tetrachlorodibenzofuran (B) in Immature Female Sprague-Dawley Rats (4 lateral substituents).

| Dose* (μmol/kg) | Uterine Wet Weight (% body wt) | Estrogen Receptor Levels (fmol/mg protein) | | Progesterone Receptor Levels (fmol/mg protein) | |
|---|---|---|---|---|---|
| | | Cytosolic | Nuclear | Cytosolic | Nuclear |
| 2A | 0.192 ± 0.013 | 131.8 ± 6.6 | 90.2 ± 5.4 | 1673 ± 117 | 835 ± 50 |
| 2B | 0.179 ± 0.009 | 183.4 ± 9.2 | 83.2 ± 4.2 | 2167 ± 152 | 866 ± 52 |
| 10A | 0.211 ± 0.019 | 125.3 ± 6.3 | 76.8 ± 3.8 | 1596 ± 112 | 685 ± 62 |
| 10B | 0.201 ± 0.008 | 151.9 ± 9.1 | 82.8 ± 5.0 | 1670 ± 117 | 701 ± 35 |
| 25A | 0.192 ± 0.004 | 117.5 ± 5.9 | 72.8 ± 3.6 | 1461 ± 102 | 631 ± 37 |
| 25B | 0.181 ± 0.002 | 137.4 ± 6.9 | 69.0 ± 4.1 | 1405 ± 98 | 697 ± 56 |
| 50A | 0.224 ± 0.012 | 107.1 ± 5.4 | 67.3 ± 4.0 | 856 ± 60 | 605 ± 66 |
| 50B | 0.172 ± 0.005 | 114.9 ± 5.8 | 69.2 ± 4.2 | 1098 ± 88 | 514 ± 41 |

*Each dose of compound was accompanied by cotreatment with 17β-estradiol (2 × 10 μg/rat).

TABLE 7

Effects of the Number of Lateral Substituents on the Antiestrogenic Potencies of Alkyl-Substituted Dibenzofurans in the Female Sprague-Dawley Rat.

| Compound (lateral substituents) | $ED_{40-60}$ for Inhibition ($\mu mol/kg$) | | | | |
|---|---|---|---|---|---|
| | Uterine Wet Weight | $PR_c$ | $PR_n$ | $ER_c$ | $ER_n$ |
| 6-ipropyl-1,3,8-triCDF (2 lateral) | 10 | 25 | 25 | 10 | 25 |
| 6-methyl-2,3,4,8-tetraCDF (3 lateral) | 10 | 2 | 10 | 2 | 2 |
| 8-methyl-2,3,7-triCDF (4 lateral) | 2 | 2 | 10 | 2 | 10 |
| 8-methyl-2,3,4,7-tetraCDF (4 lateral) | 2 | 10 | 10 | 10 | 25 |

The $ED_{40-60}$ values for the antiuterotrophic effects of these compounds varied from 2 to 10 μmol/kg (i.e. ~0.7 to 3.5 mg/kg) and the 6-isopropyl-1,3,8-triCDF was surprisingly active. The $ED_{40-60}$ values for the compounds with 4 lateral substituents were in the 2 μmol/kg range and clearly exhibited significant antiestrogenic activities. There appeared to be less consistency in the effects of these compounds on the ER receptor; however, it was apparent for most of the responses that the congeners with 3 and 4 lateral substituents were more active than the 1,3,6,8-substituted compound (2 lateral substituents).

EXAMPLE 9

Antiestrogenic Activity in MCF-7 Human Breast Cancer Cells

Cell Growth

MCF-7 cells, obtained from American Type Culture Collection (Rockville, Md.) were maintained at 37° C. in closed Corning T-25, 75 or 150 cm² flasks (Corning Glassworks, Corning, N.Y.) and passaged in logarithmic growth phase. Growth medium was Eagle's minimal essential medium containing Hanks' balanced salts, L-glutamine and non-essential amino acids (GIBCO 410–1600EB, Long Island, N.Y.), supplemented with 0.006 μg/ml insulin (Sigma, St. Louis, Mo.), 0.01M HEPES buffer (GIBCO), 5.5M glucose, 0.026M sodium bicarbonate, 0.1 mM non-essential amino acids (GIBCO), 0.1 mM essential amino acids (GIBCO), 0.01 mM sodium pyruvate (Sigma), 1.25 mg/liter amphotericin B, 2500 units penicillin/liter, 12.5 mg/liter streptomycin/gentamicin, and 5% charcoal-dextran-stripped fetal bovine serum.

For the in vitro antiestrogenicity studies, cells were treated with various concentrations of the test compounds 24 hours prior to harvesting. Interactive effects between the test compounds and 17β-estradiol were also determined.

MCF-7 cells from a single near confluent T-25 flask were incubated at 37° C. for 0.5 h prior to harvesting with 10 nM 2,4,6,7-[$^3$H]-estradiol. The medium was then decanted and the cells were rinsed once with Hanks' balanced salt solution containing 1 mM EDTA. The cells were collected by centrifugation, washed gently in 2 ml of TEDG (10 mM Tris-HCl, 1.5 mM EDTA-4Na, 10 mM dithiothreitol, 10% (v/v) glycerol, 0.8M KCl, pH 8.5 at 4° C.) buffer and homogenized in 300 μl of TEDG buffer containing protease inhibitors [soybean trypsin inhibitor 5 mg/ml (Sigma), leupeptin 1 mg/ml (Sigma), and phenylmethylsulfonyl fluoride 1 mg/ml (Sigma)] by 40 strokes of a Dounce homogenizer. The homogenate was centrifuged at 800×g for 10 minutes. The crude nuclear pellet was resuspended in 300 μl of TEDG buffer. The nuclear ER levels were then determined as described below.

Nuclear ER Levels

The nuclear extract previously obtained was incubated with 10 nM [$_3$H]-estradiol plus or minus as excess radioinert diethylstilbestrol for 1 h at 0°–4° C., with resuspension by agitation every 15 minutes. The sample was then centrifuged at 180,000×g for 30 minutes, then 200 μl of the supernatant obtained was layered onto linear 1% to 20% sucrose gradients prepared in TEDGM buffer. As before, the gradients were centrifuged at 406,000×g for 2.5 h in a vertical rotor. Following centrifugation, 30 fractions of 0.16 ml each were collected and the radioactivity in each sample was determined.

Cell Culture Conditions for Analysis of the 34-, 52- and 160-kDa Proteins

The cells were maintained in a monolayer with RPMI 1640 media (Sigma Chemical Co., St. Louis, Mo., USA) supplemented with 83 μl insulin and 5% fetal calf serum (FCS). On day −7, the cells were washed two times with phosphate buffered saline (PBS) and passage into RPMI 1640 media containing 83 μl/l insulin and 3% FCS. On day −2, the cells were washed two times with PBS and were passaged into Corning 24-well culture dishes with RPMI 1640 media containing 3% FCS, which had been treated with dextran-coated charcoal (FCS-DCC), and no insulin, at a concentration of 50,000 cells/well in 1 ml of media. On day 0, the media was removed and the cells were rinsed two times with PBS. The media was then replaced with RPMI 1640 containing 3% FCS-DCC, no insulin and one of the following chemicals: 1 nM 17β-estradiol, MCDF, TCDD, or 1 nM 17β-estradiol, +MCDF or TCDD. The dose-response effects of TCDD (0.1 to 10 nM) were also determined using a comparable protocol. The cells were allowed to incubate for 48 h. The media was changed after 24 h; 6 h prior to the termination of the experiment, the media was removed, the cells were washed two times with PBS, and the media was replaced with methionine deficient RPMI 1640 containing 3% FCS-DCC, the same chemicals and 2 μl $^{35}$S-methionine (10 mCi/ml) for a total volume of 200 μl. After 6 h, the media was removed, 10 μl was counted and the remaining media was used for analysis of secreted proteins.

The secreted proteins were analyzed by sodium dodecyl sulfate (SDS) polyacrylamide gel electrophoresis; 30 μl of the media was mixed with an equal volume of buffer containing SDS, β-mercaptoethanol, glycerol, Tris and bromophenol blue. The samples were heated for 2 minutes in a boiling water bath and 50 μl of each sample was loaded onto a 1.5 mm thick 12% acrylamide slab gel (containing 0.075% bisacrylamide) with a 3% stacking gel (containing 0.15% bisacrylamide). The gels were run at 50 mV overnight and processed for fluorography (using Enhance: Dupont) and exposed to Kodak X-OMAT film for 10 days at −80° C. The molecular weights of the proteins were estimated by their mobility relative to a set of standard proteins with known molecular weights.

The incorporation of $^{35}$S-methionine into the 34-kDa, 52-kDa and 160-kDa proteins was estimated by scanning the films using a Zeineh Soft Laser Scanning Densitometer (model SLR-20/10) from Biomedical Instruments, Inc. The percentage of the area of the scans due to the particular protein was then compared between the experimental and control samples and the results are presented as means ± SD for at least three samples per treatment group.

Previous studies have demonstrated that TCDD exhibit antiestrogenic activity in human breast cancer cell lines (Harris et al., Cancer Res., 50:3579–358, 1990; Biegel and Safe, J. Steroid Bioch. & Molec. Biol. 37:725–732 (1990)). For example, TCDD inhibits 17β-estradiol-induced growth of MCF-7 human breast cancer cells. In addition to their growth stimulatory effects, estrogens elicit a broad spectrum of responses in ER-responsive cell lines such as the MCF-7 cells and this includes the enhanced secretion of the 34-, 52- and 160-kDa proteins. The former two proteins have been identified as cathepsin D (an aspartyl protease) and pro-cathespin D, and the presence of these two proteins in primary human breast tumors is correlated with a poor prognosis for disease-free survival (Spyratos et al., Lancet, pp. 115–118, 1989; Tandon et al., N. Eng. J Med., 322:297–302, 1990). The results summarized in Table 8 show that 17β-estradiol treatment caused a 3.72-, 4.97- and 3.81-fold increase in the secretion of the 34- 52- and 160-kDa proteins, respectively, whereas 10 nM TCDD alone did not significantly affect the secretion of these proteins in MCF-7 cells. However, in the cells treated with TCDD plus 17β-estradiol, it was apparent that TCDD significantly inhibited the hormone-induced secretion of all three proteins (Biegel and Safe, J Ster. Bloch. & Molec. Biol, 37:725–732 (1990). In contrast, TCDD, 17β-estradiol and TCDD plus 17β-estradiol did not affect the secretion of these proteins in the Ah non-responsive MDA-MB-231 cell line. (Biegel and Safe, J Ster. Bioch. & Molec. Biol, 37:725–732 (1990).

complexes which are maximized within 1 h after addition of the hormone and decrease thereafter (Harris et al., Cancer Res., 50:3579–3584, 1990). Cotreatment of the cells with 10 nM TCDD plus [$^3$H]-17β-estradiol did not affect the levels of occupied nuclear ER complex; however, pretreatment with TCDD 6 or 12 hours prior to addition of the radiolabeled hormone resulted in a significant downregulation of occupied nuclear ER levels as determined by velocity sedimentation analysis of the nuclear extracts. Moreover, using commercially-available antibodies to the human ER (Abbott Laboratories, North Chicago, Ill., USA), it was shown that the concentration-dependent decrease in ER binding was paralleled by a decrease in immunoreactive ER protein. The comparative effects of both TCDD (10 nM) and MCDF (100 nM) on the downregulation of nuclear ER in MCF-7 cells has been investigated and it was apparent from the results that both MCDF and TCDD caused a decrease in nuclear ER levels. (Zacharewski, et al. Toxicol. Appl. Pharmacol 113, 311–318, 1992)

TABLE 8

Concentration-Dependent Effects of TCDD on the 17β-Estradiol-Induced Secretion of the 34-, 52- and 160-kDa Proteins in MCF-7 Cells.

| Treatment | Concentration of the $^{33}$S-labeled secreted proteins as a percent of the values for control calls | | |
|---|---|---|---|
| (conc, nM)[a] | 160-kDa | 52-kDa | 34-kDa |
| 17β-Estradiol | 371 ± 27.1 | 225 ± 27.8 | 282 ± 17.6 |
| TCDD (0.1) | 92.8 ± 5.16 | 103 ± 4.35 | 94.5 ± 133 |
| TCDD (0.01) | 90.4 ± 17.2 | 93.1 ± 15.5 | 85.7 ± 11.9 |
| TCDD (0.001) | 94.3 ± 3.00 | 87.7 ± 4.89 | 95.2 ± 12.8 |
| TCDD (0.0001) | 97.4 ± 2.73 | 103 ± 6.63 | 86.5 ± 8.56 |
| 17β-Estradiol + TCDD (0.0001) | 321 ± 29.0 | 164 ± 20.3 | 255 ± 37.8 |
| 17β-Estradiol + TCDD (0.001) | 167 ± 31.3[b] | 126 ± 4.62[b] | 151 ± 20.7[b] |
| 17β-Estradiol + TCDD (0.01) | 127 ± 21.0[b] | 103 ± 4.39[b] | 94.2 ± 24.0[b] |
| 17β-Estradiol + TCDD (0.1) | 94.3 ± 5.23[b] | 94.4 ± 3.86[b] | 94.9 ± 11.4[b] |

[a]The concentration of 17β-estradiol was 1 nM in all experiments.
[b]Significantly lower (P < 0.01) than cells treated with 17β-estradiol alone.

In a parallel study, I examined the antiestrogenic activity of MCDF as an antiestrogen in MCF-7 human breast cancer cells. The results of studies with MCDF also clearly show that this compound inhibits the 17β-estradiol-induced growth of MCF-7 cells. (Zacharewski, et al., Toxicol. Appl. Pharmacol. 113:311–318 (1992)). Like TCDD, MCDF also inhibits the 17β-estradiol-induced secretion of the 34-, 52- and 160-kDa proteins in MCF-7 human breast cancer cells (Table 9).

TABLE 9

MCDF as an Antiestrogen: Inhibition of the 17β-estradiol-Induced Secretion of the 32-,54- and 160-kDa Proteins. Zacharewski, et al., Toxicol. Appl. Pharmacol. 113:311–318 (1992)

| Treatment | Protein Secretion (% of Control) | | |
|---|---|---|---|
| | 34-kDa | 52-kDa | 160-kDa |
| Control | 100 | 100 | 100 |
| 17β-Estradiol (1 nM) | 201 | 143 | 228 |
| MCDF (100 nM) | 80 | 96 | 72 |
| 17β-Estradiol + MCDF | 78 | 87 | 76 |

Treatment of MCF-7 cells with 1 nM [$^3$H]-17β-estradiol resulted in the rapid formation of radiolabeled nuclear ER

EXAMPLE 10

Antiestrogenic activities of 6-methyl 1,3,8-tricholordibenzofuran.

Twenty-five day old female Sprague/Dawley rats with at least four rats in each treatment group were injected with either corn oil (control), 17β-estradiol (5 μM/rat, sidx2 days), TCDD, MCDF, estradiol plus TCDD or estradiol plus MCDF (see Tables for dose levels). TCDD or MCDF was co-administered with a second dose of estradiol and the animals were killed 48-hours later. A second group of animals was similarly treated with corn oil, TCDD, MCDF, or TCDD plus MCDF, all administered in corn oil at 10 ml/kg and terminated 72 hours later.

The animals were terminated by cervical dislocation. Livers were perfused with ice-cold TEDG buffer (10 mM Tris-HCl, 1.5 mM EDTA-4Na, 1 mM dithiothreitol, 10% glycerol (v/v), pH 7.4). Following perfusion in situ, livers were removed, weighed, and homogenized in ice-cold TEDG buffer. Uteri were also removed, weighed, and homogenized in ice-cold buffer. The homogenates were then centrifuged at 800×g (200 rpm) for 15 minutes and the nuclear pellets were stored at −80° C. The supernatants were further centrifuged at 180,000×g for 1.5 hour. The cytosolic supernatant was also stored at −80° C. Estrogen and progesterone receptor levels were determined within 7 days.

Estrogen and progesterone receptor levels were determined by the hydroxyapatite assay as described by Clark et al. (J. Steroid, Biochem., 16, 323–328 (1982)). Briefly, samples were incubated with 10nM [$^3$H]17β-estradiol or [$^3$H]R5020 with or without 200-fold excess cold DES or progesterone, respectively. Following the incubations, samples were counted and specific binding was calculated by subtraction of nonspecific from total binding. Assuming one steroid molecule binds to one estrogen/progesterone receptor, the number of moles of receptor can be calculated given the specific activity of the radioligand. The data presented in Tables 10–13 are means ± SD using at least four animals per treatment group. Significant differences were determined by ANOVA.

The results of these experiments are shown in Tables 10–12 below.

TABLE 10

EFFECTS OF TCDD AND MCDF ON HEPATIC AND UTERINE ER AND PR LEVELS IN THE FEMALE RAT

| Treatment | Hormone receptor levels (fmol/mg protein)[a] | | | |
|---|---|---|---|---|
| (dose, μmol/kg) | ERc | ERn | PRc | PRn |
| | Uterine levels | | | |
| Control | 147.8 ± 24.1 | 16.4 ± 2.1 | 1204 ± 61.1 | 410 ± 46.1 |
| TCDD (0.032) | 121.6 ± 11.3 | 15.1 ± 1.0 | 109 ± 71.3 | 360 ± 39.8 |
| TCDD (0.128) | 109.6 ± 12.0* | 14.0 ± 1.4 | 903 ± 49.3 | 251 ± 30.1* |
| TCDD (0.256) | 92.1 ± 8.2* | 10.6 ± 0.6* | 82 ± 30.2* | 190 ± 14.2* |
| MCDF (10) | 137.7 ± 11.6 | 15.8 ± 1.9 | 980 ± 34.6* | 390 ± 31.6 |
| MCDF (50) | 110.3 ± 6.6* | 13.2 ± 2.1 | 886 ± 20.1* | 290 ± 30.2* |
| MCDF (100) | 90.2 ± 11.2* | 11.5 ± 1.0* | 811 ± 26.4* | 240 ± 26.1* |
| | Hepatic levels | | | |
| Control | 6.9 ± 0.4 | 6.4 ± 0.8 | 80.4 ± 7.3 | 9.4 ± 1.3 |
| TCDD (0.032) | 4.6 ± 0.8* | 5.4 ± 0.7 | 70.2 ± 7.9 | 8.3 ± 1.2 |
| TCDD (0.128) | 3.4 ± 0.4* | 3.4 ± 0.4* | 61.0 ± 5.4* | 7.1 ± 0.9* |
| TCDD (0.256) | 1.7 ± 0.3* | 2.3 ± 0.6* | 38.3 ± 3.9* | 5.9 ± 1.1* |
| MCDF (10) | 6.6 ± 0.5 | 6.1 ± 1.0 | 74.3 ± 8.1 | 8.9 ± 1.5 |
| MCDF (50) | 4.6 ± 0.8* | 3.5 ± 0.6* | 66.0 ± 7.1 | 7.6 ± 1.0 |
| MCDF (100) | 3.1 ± 0.3* | 3.1 ± 0.7* | 40.2 ± 3.2* | 6.8 ± 1.0* |

[a]Data expressed as means ± SD.
*Significantly different from controls (p < 0.01).

TABLE 11

EFFECTS OF TCDD AND MCDF ON HEPATIC AND UTERINE ER AND PR LEVELS IN FEMALE RATES TREATED WITH ESTRADIOL

| Treatment | Hormone receptor levels (fmol/mg protein)[a] | | | |
|---|---|---|---|---|
| (dose, μmol/kg) | ERc | ERn | PRc | PRn |
| | Uterine levels | | | |
| Control | 101 ± 5.9 | 18.3 ± 1.0 | 1158 ± 110.2 | 490 ± 24.3 |
| Estradiol (E-2) | 215 ± 7.9* | 31.4 ± 2.0* | 2593 ± 70.2* | 804 ± 31.2* |
| TCDD (0.256) | 57.8 ± 6.3* | 11.7 ± 0.8* | 898.0 ± 49.2* | 180 ± 9.9* |
| MCDF (100 μmol/kg) | 67.8 ± 2.5* | 13.0 ± 1.1* | 805.3 ± 29.0* | 205 ± 10.6* |
| E-2 + TCDD | 82.8 ± 5.4** | 17.4 ± 1.0** | 811.3 ± 27.1** | 511 ± 19.3** |
| E-2 + MCDF | 93.5 ± 4.0** | 18.5 ± 1.2** | 941.2 ± 45.1** | 602 ± 11.4** |
| | Hepatic levels | | | |
| Control | 6.5 ± 1.5 | 5.1 ± 1.0 | 104.8 ± 8.4 | 10.3 ± 0.9 |
| Estradiol (E-2) | 13.5 ± 1.9* | 12.4 ± 1.1* | 142.6 ± 9.8* | 14.2 ± 1.1 |
| TCDD (0.256) | 2.2 ± 0.8* | 2.4 ± 0.4* | 61.9 ± 7.3* | 5.9 ± 0.4* |
| MCDF (100 μmol/kg) | 3.7 ± 1.1* | 3.1 ± 0.2* | 60.6 ± 8.4* | 5.1 ± 1.0* |
| E-2 + TCDD | 6.8 ± 1.0** | 4.0 ± 0.8** | 110.3 ± 8.3** | 6.8 ± 1.3* |
| E-2 + MCDF | 8.1 ± 1.2** | 3.6 ± 0.9** | 108.9 ± 11.1** | 6.4 ± 1.0** |

[a]Data expressed as means ± SD.
*Values significantly different from controls (p < 0.01).
**Values significantly different from estradiol.

TABLE 12

Effects of TCDD and MCDF on Uterine Wet Weights
In Female Rats Treated With Estradiol

| Treatment (dose, μmol/kg) | Uterine Wet Weight (as % body wt) |
|---|---|
| Corn Oil | 0.154 ± 0.010 |
| Estradiol (E-2) | 0.322 ± 0.035 |
| TCDD (0.256) | 0.086 ± 0.011* |
| MCDF (100) | 0.090 ± 0.113* |
| E-2 + TCDD | 0.245 ± 0.026** |
| E-2 + MCDF | 0.255 ± 0.031** |

*Significantly different from controls ($p < 0.01$).
**Significantly different from estradiol-treated ($p < 0.01$).

Dose levels of 50 and 100 μmol/kg MCDF caused a dose dependent decrease in constitutive uterine hepatic estrogen receptors and progesterone receptor levels (Table 10). In addition, the uterine and hepatic estrogen receptors and progesterone receptor levels in rats treated with MCDF plus estradiol were 43, 59, 36 and 75% respectively, of the corresponding levels observed in rats treated with 17β-estradiol alone (Table 11). As demonstrated in Table 12 MCDF also significantly decreased uterine wet weights compared to the corn oil treated animals, and in the co-treated animals MCDF partially inhibited the estradiol induced increase in uterine wet weight. This reduction of estrogen receptors and uterine wet weights is indicative of antiestrogenic activity. The amounts of these compounds which produce the antiestrogenic activity have not demonstrated any toxicity in parallel toxicity studies.

EXAMPLE 11

MCF-7 cells, obtained from American Type Culture Collection (Rockville, Ma.), were maintained at 37° C. in closed Corning T-25, 75 or 150 cm$^2$ flasks (Corning Glassworks, Corning, N.Y.) and passaged in logarithmic growth phase. Growth medium was Eagle's minimal essential medium containing Hanks' balanced salts, L-glutamine and non-essential amino acids (GIBCO 410-1600EB), supplemented with 0,006 μg/ml insulin (Sigma), 0.01M HEPES buffer (GIBCO), 5.5M glucose, 0.026M sodium bicarbonate, 0.1 mM non-essential amino acids (GIBCO), 0.1 mM essential amino acids (GIBCO), 0.01 mM sodium pyruvate (Sigma), 1.25 mg/liter amphotericin B, 2500 units penicillin/liter, 12.5 mg/liter streptomycin/gentamycin and 5% charcoal-dextran-stripped fetal bovine serum.

For the 2,3,7,8-TCDD antiestrogenicity studies, cells were treated 24 hours prior to harvesting with various concentrations of 2,3,7,8-TCDD (0.1 nM to 100 nM 2,3,7,8-TCDD). Interactive effects between 2,3,7,8-TCDD and estradiol were conducted using these same concentrations of 2,3,7,8-TCDD and 10 nM estradiol. To study possible antagonistic/antiestrogenic effects of 6-methyl-1,3,8-trichlorodibenzofuran (MCDF), varying concentrations from 15 to 150 μM were added or coadministered to the MCF-7 cells.

MCF-7 cells from a single near confluent T-25 flask were incubated at 37° C. for 0.5 hours prior to harvesting with 10 nM 2,4,6,7-[$^3$H]-estradiol. The medium was then decanted and the cells were rinsed once with Hanks' balanced salt solution containing 1 mM EDTA. The cells were collected by centrifugation, washed gently in 2 ml of TEDG buffer and homogenized in 300 μl of TEDG buffer containing protease inhibitors [soybean trypsin inhibitor 5 mg/ml (Sigma), leupetin 1 mg/ml (Sigma), and phenylmethylsulfonyl fluoride 1 mg/ml (Sigma) by 40 strokes of a Dounce homogenizer. The homogenate was centrifuged at 800×g for 10 minutes. The crude nuclear pellet was resuspended in 300 μl of TEDGK buffer (10 mM Tris-HCl, 1.5 mM EDTA-4Na, 10 mM dithiothreitol, 10% (v/v) glycerol, 0.8 M KCl, pH 8.5 at 4° C.). The nuclear ER levels were then determined as described below.

The nuclear extract previously obtained was incubated with 10 nM [$^3$H]-estradiol plus or minus radioinert diethylstilbestrol for 1 hour at 0–4° C., with resuspension by agitation every 15 minutes. The sample was then centrifuged at 180,000×g for 30 minutes, then 200 μl of the supernatant obtained was layered onto linear 1–20% sucrose gradients prepared in TEDGMK buffer. As before, the gradients were centrifuged at 406,000×g for 2.5 hours in a vertical rotor. Following centrifugation, 30 fractions of 0.16 μl were collected and the radioactivity in each sample was determined.

The dose response data following MCDF treatment are given in Tables 13–14. MCDF significantly decreased ERn levels in the MCF-7 cells. The combined effects of MCDF plus 2,3,7,8-TCDD was clearly not additive. The ERn levels for the combined treatment were not significantly different than those observed after treatment with either 2,3,7,8-TCDD or MCDF.

TABLE 13

Interactive Effects of Estradiol, 2,3,7,8-TCDD and MCDF on ERn in MCF-7 Cells

| Treatment (dose) | Coadministered with (dose) | ERn fmol/mg protein (S.D.) |
|---|---|---|
| control | — | 199.8 (10.2) |
| estradiol (10 nM) | MCDF (15 μM) | 113.4 (3.9)* |
| estradiol (10 nM) | MCDF (50 μM) | 103.4 (17.6)* |
| estradiol (10 nM) | MCDF (100 μM) | 106.4 (7.9)* |
| estradiol (10 nM) | 2,3,7,8-TCDD (10 nM) plus MCDF (15 nM) | 133.1 (14.3)* |
| estradiol (10 nM) | 2,3,7,8-TCDD (10 nM) plus MCDF (50 μM) | 122.3 (5.5)* |
| estradiol (10 nM) | 2,3,7,8-TCDD (10 nM) plus MCDF (100 μM) | 125.5 (9.7)* |
| estradiol (10 nM) | 2,3,7,8-TCDD (25 nM) plus MCDF (15 μM) | 132.6 (2.1)* |
| estradiol (10 nM) | 2,3,7,8-TCDD (25 nM) plus MCDF (50 μM) | 130.5 (5.3)* |
| estradiol (10 nM) | 2,3,7,8-TCDD (25 μM) plus MCDF (100 μM) | 123.8 (8.3)* |

*Significantly different from control ($p < 0.01$).

TABLE 14

Antiestrogenic Activity in MCF-7 Cells
Effects of MCDF and Cotreatment of MCDF
Plus 2,3,7,8-TCDD on ERn in MCF-7 Cells.

| Treatment (dose) | Coadministered with (dose) | ERn fmol/mg protein (S.D.) |
|---|---|---|
| control | — | 222.2 (5.6) |
| MCDF (15 μM) | — | 207.5 (6.6)* |
| MCDF (50 μM) | — | 171.6 (13.7)* |
| MMF (75 μM) | — | 141.8 (13.6)* |
| MCDF (100 μM) | — | 135.8 (4.5)* |
| MCDF (150 μM) | — | 114.2 (7.9)* |
| control | | 225.5 (22.6) |
| 2,3,7,8-TCDD (10 nM) | MCDF (15 μM) | 147.5(9.6)* |
| 2,3,7,8-TCDD (10 nM) | MCDF (50 μM) | 136.0(14.7)* |
| 2,3,7,8-TCDD (10 nM) | MCDF (75 μM) | 133.1(10.4)* |
| 2,3,7,8-TCDD (10 nM) | MCDF (100 μM) | 123.1(7.1)* |
| 2,3,7,8-TCDD (10 nM) | MCDF (150 μM) | 129.3(2.9)* |
| 2,3,7,8-TCDD (25 nM) | MCDF (15 μM) | 146.9(9.6)* |
| 2,3,7,8-TCDD (25 nM) | MCDF (50 μM) | 85.5(16.5)* |
| 2,3,7,8-TCDD (25 nM) | MCDF (75 μM) | 91.3(9.7)* |

TABLE 14-continued

Antiestrogenic Activity in MCF-7 Cells
Effects of MCDF and Cotreatment of MCDF
Plus 2,3,7,8-TCDD on ERn in MCF-7 Cells.

| Treatment (dose) | Coadministered with (dose) | ERn fmol/mg protein (S.D.) |
|---|---|---|
| 2,3,7,8-TCDD (25 nM) | MCDF (100 μM) | 100.5 (10.4)* |
| 2,3,7,8-TCDD (25 nM) | MCDF (150 μM) | 108.1(18.1)* |

*Significantly different from control (p < 0.01).

Many other variations and modifications may be made in the techniques hereinbefore described, by those having experience in this technology, without departing from the concept of the present invention. Accordingly, it should be clearly understood that the methods described in the foregoing description are illustrative only, and not intended as a limitation on the scope of the invention.

What is claimed is:

1. A method of inhibiting estrogen activity comprising administering a biologically active amount of a compound of the formula:

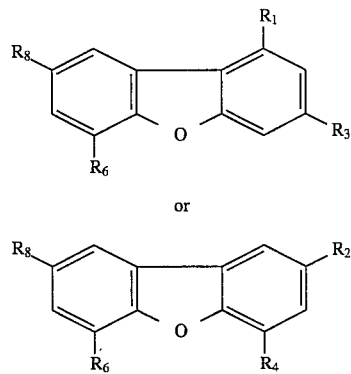

wherein $R_1$, $R_3$, $R_6$ and $R_8$ or $R_2$, $R_4$, $R_6$ and $R_8$ are individually and independently a hydrogen or a substituent selected from the group consisting of chlorine, fluorine and bromine, and a linear or branched alkyl group of one to four carbons, said compound having at least one alkyl substituent and at least two halogen substituents.

2. A method according to claim 1 wherein the halogen is chlorine.

3. A method according to claim 1 wherein the alkyl substituent is selected from the group consisting of methyl, ethyl and propyl.

4. A method according to claim 1 wherein $R_6$ is an alkyl substituent and $R_1$, $R_3$, and $R_8$ are selected from the group consisting of chlorine, fluorine and bromine.

5. A method according to claim 5 wherein the alkyl substituent is methyl.

6. A method according to claim 1 wherein $R_8$ is an alkyl substituent and $R_1$, $R_3$, and $R_6$ are selected from the group consisting of chlorine, fluorine and bromine.

7. A method according to claim 6 wherein the alkyl substituent is methyl.

8. A method according to claim 1 wherein $R_6$ is an alkyl and $R_2$, $R_4$, and $R_8$ are selected from the group consisting of chlorine, fluorine and bromine.

9. A method according to claim 8 wherein the alkyl substituent is methyl.

10. A method according to claim 1 wherein $R_8$ is an alkyl substituent and $R_2$, $R_4$, and $R_6$ are selected from the group consisting of chlorine, fluorine and bromine.

11. A method according to claim 10 wherein the alkyl substituent is methyl.

12. A method of inhibiting estrogen activity comprising administering a biologically active amount of a compound selected from the group consisting of 6-methyl-1,3,8-trichlorodibenzofuran, 8-methyl-1,3,6-trichlorodibenzofuran, 6-ethyl-1,3,8-trichlorodibenzofuran, 6-propyl-1,3,8-trichlorodibenzofuran, 6-methyl-2,3,8-trichlorodibenzofuran, 6-methyl-2,3,4,8-tetrachlorodibenzofuran, 8-methyl-1,3,7-trichlorodibenzofuran, 8-methyl-1,2,4,7-tetrachlorodibenzofuran, 8-methyl-2,3,7-trichlorodibenzofuran, and 8-methyl-2,3,7-tetrachlorodibenzofuran.

13. A method of inhibiting estrogen activity comprising administering a biologically active amount of a compound of the formula:

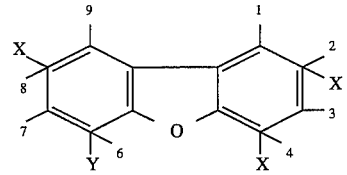

wherein X, individually and independently, is a hydrogen or a substituent selected from the group consisting of bromine, chlorine, fluorine, and a linear or branched alkyl group of about one to about four carbons, with no more than one X being a hydrogen;

wherein Y is a substituent selected from the group consisting of bromine, chlorine, fluorine, and a linear or branched alkyl group of about one to about four carbons;

said compound having at least one alkyl substituent and at least two halogen substituents.

14. A method of inhibiting estrogen activity comprising administering a biologically active amount of a compound of the formula:

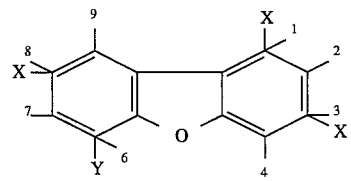

wherein X, individually and independently, is a hydrogen or a substituent selected from the group consisting of bromine, chlorine, fluorine, and a linear or branched alkyl group of about one to about four carbons, with no more than one X being a hydrogen;

wherein Y is a substituent selected from the group consisting of bromine, chlorine, fluorine, and a linear or branched alkyl group of about one to about four carbons; said compound having at least one alkyl substituent and at least two halogen substituents.

15. A method of treating estrogen-dependent tumors comprising administering a biologically active amount of a compound of the formula

31

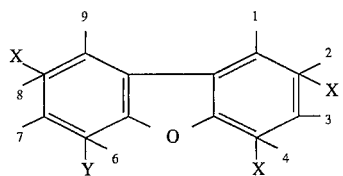

wherein X, individually and independently, is a hydrogen or a substituent selected from the group consisting of bromine, chlorine, fluorine, and a linear or branched alkyl group of about one to about four carbons, with no more than one X being a hydrogen;

wherein Y is a substituent selected from the group consisting of bromine, chlorine, fluorine, and a linear or branched alkyl group of about one to about four carbons; and said compound having at least one alkyl substituent and at least two halogen substituents.

16. A method of treating estrogen-dependent tumors comprising administering a biologically active amount of a compound of the formula

32

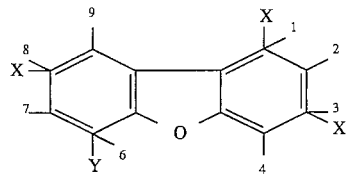

wherein X, individually and independently, is a hydrogen or a substituent selected from the group consisting of bromine, chlorine, fluorine, and a linear or branched alkyl group of about one to about four carbons, with no more than one X being a hydrogen;

wherein Y is a substituent selected from the group consisting of bromine, chlorine, fluorine, and a linear or branched alkyl group of about one to about four carbons; and said compound having at least one alkyl substituent and at least two halogen substituents.

\* \* \* \* \*

UNITED STATES PATENT AND TRADEMARK OFFICE
CERTIFICATE OF CORRECTION

PATENT NO. : 5,516,790
DATED : May 14, 1996
INVENTOR(S) : Stephen H. Safe

It is certified that error appears in the above-indentified patent and that said Letters Patent is hereby corrected as shown below:

TITLE PAGE

In OTHER PUBLICATIONS:

"Denomme, et al., chemc.-Boil. Interactions" should read
--Denomme, et al., chemc.-Biol. Interactions--.

"Kociba, et al., Toxicol. Appl. Pharmacol, 65, p. 170 (1982)." should read
--Kociba, et al., Toxicol. Appl. Pharmacol, 46, p. 279 (1978).--.

"Ramalingan et al., Chlorinated Dioxins Dibenzofurens" should read
--Ramalingan et al., Chlorinated Dioxins Dibenzofurans--.

"Astroff et al., C.A., 110:19,507g (1989)..., 95(3), 435-433 (1988)." should read
--Astroff et al., C.A., 110:19,507g (1989)..., 95(3), 435-43 (1988).--.

"Yao et al., C.A., 111: 168,9646(1989)-Abstract of Toxxical." should read
--Yao et al., C.A., 111: 168,9646(1989)-Abstract of Toxical.--.

Column 1, line 8 and 9, "a continuation of" should read --a divisional of--.

Column 5, line 53, "active 15 amount" should read --active amount--.

Column 7, line 13 and 14, "selected 35 from" should read --selected from--.

Column 7, line 35, "Arch. Blochem. Biophys." should read --Arch. Biochem. Biophys.--.

Column 7, line 64, "Arch. Blochem. Biophys." should read --Arch. Biochem. Biophys.--.

UNITED STATES PATENT AND TRADEMARK OFFICE
CERTIFICATE OF CORRECTION

Page 2 of 4

PATENT NO. : 5,516,790
DATED : May 14, 1996
INVENTOR(S) : Stephen H. Safe

It is certified that error appears in the above-indentified patent and that said Letters Patent is hereby corrected as shown below:

Column 9 correct DIAGRAM 3:

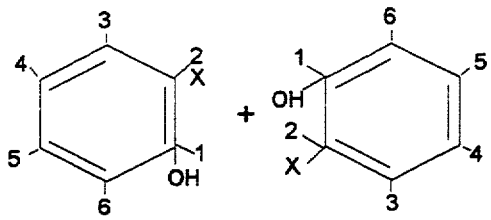

Column 16, Table 1, Column "Compound", Row 4, "+ 3-2" should read --+ E-2--.

Column 16, Table 1, Column "Compound", Row 18, "+ B-2" should read --+ E-2--.

Column 16, Table 1, Column "Estrogen Receptor Levels", Subcolumn "Cytosolic",
    Row 4, "78.9 ± 79.1" should read --78.9 ± 9.1--.
    Row 6, "65.9 ± 77.5" should read --65.9 ± 7.5--.
    Row 10, "188.7 ± 74.0" should read --188.7 ± 4.0--.
    Row 12, "104.3 ± 77.1" should read --104.3 ± 7.1--.
    Row 16, "135.5 ± 78.1" should read --135.5 ± 8.1--.

Column 16, Table 1, Column "Estrogen Receptor Levels", Subcolumn "Nuclear",
    Row 2, "79.3 ± 72.5" should read --79.3 ± 2.5--.
    Row 4, "43.3 ± 73.4" should read --43.3 ± 3.4--.
    Row 6, "20.8 ± 70.5" should read --20.8 ± 0.5--.

Column 17, Table 2, Column "Compound", Row 4, "+ B-2" should read --+ E-2--.

UNITED STATES PATENT AND TRADEMARK OFFICE
CERTIFICATE OF CORRECTION

PATENT NO. : 5,516,790
DATED : May 14, 1996
INVENTOR(S) : Stephen H. Safe

It is certified that error appears in the above-indentified patent and that said Letters Patent is hereby corrected as shown below:

Column 17, Table 3, Column "Compound", Row 10, "+ B-2" should read --+ E-2--.

Column 18, line 30, "decreasing EC50 values" should read --decreasing $EC_{50}$ values--.

Column 22, line 19, "83 µl insulin" should read --83 µg/l insulin--.

Column 22, line 64, "Res., 50:3579-358, 1990" should read --Res., 50:3579-3584, 1990--.

Column 23, line 17, "J Ster. Bloch. & Molec." should read --J Ster. Bioch. & Molec.--.

Column 23, Table 8, Column "52-kDa", Row 9, "94.4 ± 3.86$^b$" should read --94.4 ± 3.80$^b$--.

Column 26, Table 10, Column "PRc", Row 13, "66.0 ± 7.1" should read --66.8 ± 7.1--.

Column 27, line 42, "with 0,006 µg/ml" should read --with 0.006 µg/ml--.

Column 28, Table 14, Column "ERn...", Row 1, "222.2 (5.6)" should read --221.2 (5.6)--.

Column 28, Table 14, Column "ERn...", Row 9, "136.8(14.7)" should read -136.0(14.7)--.

Column 29, line 13, "be 35 made" should read --be made--.

UNITED STATES PATENT AND TRADEMARK OFFICE
CERTIFICATE OF CORRECTION

PATENT NO. : 5,516,790
DATED : May 14, 1996
INVENTOR(S) : Stephen H. Safe

It is certified that error appears in the above-indentified patent and that said Letters Patent is hereby corrected as shown below:

Column 30, line 18, "8-methyl-2,3,7-tetrachlorodibenzofuran" should read
--8-methyl-2,3,4,7-tetrachlorodibenzofuran--.

Signed and Sealed this

First Day of October, 1996

Attest:

BRUCE LEHMAN

Attesting Officer

Commissioner of Patents and Trademarks